US012597507B2

(12) United States Patent
    Kwong et al.

(10) Patent No.:  US 12,597,507 B2
(45) Date of Patent:        Apr. 7, 2026

(54) SYSTEM AND METHOD FOR COMPRESSING AND/OR RECONSTRUCTING MEDICAL IMAGE

(71) Applicant: City University of Hong Kong, Kowloon (HK)

(72) Inventors: Sam Tak Wu Kwong, Kowloon (HK); Xiangrui Liu, Kowloon (HK); Shiqi Wang, Kowloon (HK)

(73) Assignee: City University of Hong Kong, Kowloon (HK)

( * ) Notice: Subject to any disclaimer, the term of this patent is extended or adjusted under 35 U.S.C. 154(b) by 0 days.

(21) Appl. No.: 18/625,551

(22) Filed: Apr. 3, 2024

(65) Prior Publication Data

US 2024/0428927 A1     Dec. 26, 2024

Related U.S. Application Data

(60) Provisional application No. 63/509,413, filed on Jun. 21, 2023.

(51) Int. Cl.
    *G16H 30/40*        (2018.01)
    *H04N 19/105*       (2014.01)
    (Continued)

(52) U.S. Cl.
    CPC ........... *G16H 30/40* (2018.01); *H04N 19/105* (2014.11); *H04N 19/12* (2014.11); *H04N 19/174* (2014.11)

(58) Field of Classification Search
    None
    See application file for complete search history.

(56) References Cited

U.S. PATENT DOCUMENTS 6,937,767 B1      8/2005  Burak et al.
10,790,056 B1 *   9/2020  Accomazzi ......... H04L 67/1097
                  (Continued)

OTHER PUBLICATIONS

Fabian Mentzer, Eirikur Agustsson, Michael Tschannen, Radu Timofte, and Luc Van Gool. Practical Full Resolution Learned Lossless Image Compression. In Proceedings of the IEEE/CVF conference on Computer Vision and Pattern Recognition, pp. 10629-10638, 2019.

(Continued)

*Primary Examiner* — Chikaodili E Anyikire
(74) *Attorney, Agent, or Firm* — Renner, Kenner, Greive, Bobak, Taylor & Weber

(57)        ABSTRACT

A method for compressing a 3D medical image includes the steps of receiving a 3D medical image, partitioning the 3D medical image into a plurality of first slices, encoding the plurality of the first slices by a lossy codec into first bitstreams, decoding the first bitstreams by the lossy codec to obtain a plurality of second slices, computing a plurality of residues by comparing the plurality of the first slices and the plurality of the second slices, encoding the plurality of the residues by a lossless codec to obtain a plurality of encoded residues, and outputting the first bitstreams and the plurality of the encoded residues as compressed image data. Each residue corresponds to one of the first slices and its corresponding second slice. Experimental results on prevailing 3D medical image datasets demonstrate that the proposed method achieves promising compression performance and outperforms state-of-the-art methods.

17 Claims, 12 Drawing Sheets

(51) Int. Cl.
　H04N 19/12 　　(2014.01)
　H04N 19/174 　(2014.01)

(56) References Cited

U.S. PATENT DOCUMENTS

| | | | |
|---|---|---|---|
| 2003/0023158 A1 | 1/2003 | Danielsson et al. | |
| 2009/0228299 A1* | 9/2009 | Kangarloo | G16H 30/40 |
| | | | 707/999.005 |
| 2010/0080476 A1 | 4/2010 | Khorasani et al. | |
| 2014/0079302 A1 | 3/2014 | Sato et al. | |
| 2015/0172681 A1 | 6/2015 | Kim et al. | |
| 2017/0180737 A1* | 6/2017 | Ye | H04N 19/70 |
| 2017/0280145 A1* | 9/2017 | Kubota | H04N 19/176 |
| 2023/0337907 A1* | 10/2023 | Prince | A61B 3/102 |
| 2024/0028639 A1* | 1/2024 | Ezrielev | G06F 16/538 |

OTHER PUBLICATIONS

Kumar, Pardeep, and Ashish Parmar, "Versatile Approaches for Medical Image Compression: A Review," Procedia Computer Science, 2020, pp. 1380-1389.

Doukas, Charalampos, and Ilias Maglogiannis, "Region of Interest Coding Techniques for Medical Image Compression," IEEE Engineering in Medicine and Biology Magazine, 2007, pp. 29-35.

Wang, Jun, and Kun Huang, "Medical Image Compression by Using Three-dimensional Wavelet Transformation." IEEE Transactions on Medical Imaging, 1996, pp. 547-554.

Ström, Jacob, and Pamela C. Cosman, "Medical Image Compression with Lossless Regions of Interest," Signal Processing, 1997, pp. 155-171.

Kaur, Manpreet, and Vikas Wasson, "ROI Based Medical Image Compression for Telemedicine Application," Procedia Computer Science, 2015, pp. 579-585.

Shen, Liang, and Rangaraj M. Rangayyan, "A Segmentation-based Lossless Image Coding Method for High-resolution Medical Image Compression," IEEE Transactions on Medical imaging, 1997, pp. 301-307.

P. Rajpurkar, E. Chen, O. Banerjee, and E. J. Topol, "AI in health and medicine," Nature Medicine, vol. 28, No. 1, pp. 31-38, 2022.

Z. Zheng, J. S. Lauritzen, E. Perlman, C. G. Robinson, M. Nichols, D. Milkie, O. Torrens, J. Price, C. B. Fisher, N. Sharifi et al., "A complete electron microscopy volume of the brain of adult *Drosophila melanogaster*," Cell, vol. 174, No. 3, pp. 730-743, 2018.

Y. Zhang, Y. Wei, Q. Wu, P. Zhao, S. Niu, J. Huang, and M. Tan, "Collaborative unsupervised domain adaptation for medical image diagnosis," IEEE Transactions on Image Processing, vol. 29, pp. 7834-7844, 2020.

S. Zhou, D. Nie, E. Adeli, J. Yin, J. Lian, and D. Shen, "High-resolution encoder-decoder networks for low-contrast medical image segmentation," IEEE Transactions on Image Processing, vol. 29, pp. 461-475, 2019.

W. Tang, F. He, Y. Liu, and Y. Duan, "MATR: Multimodal medical image fusion via multiscale adaptive transformer," IEEE Transactions on Image Processing, vol. 31, pp. 5134-5149, 2022.

D. Zhang, G. Huang, Q. Zhang, J. Han, J. Han, Y. Wang, and Y. Yu, "Exploring task structure for brain tumor segmentation from multi-modality MR images," IEEE Transactions on Image Processing, vol. 29, pp. 9032-9043, 2020.

A. Esteva, A. Robicquet, B. Ramsundar, V. Kuleshov, M. DePristo, K. Chou, C. Cui, G. Corrado, S. Thrun, and J. Dean, "A guide to deep learning in healthcare," Nature Medicine, vol. 25, No. 1, pp. 24-29, 2019.

J. Ma, H. Xu, J. Jiang, X. Mei, and X.-P. Zhang, "DDcGAN: A dual-discriminator conditional generative adversarial network for multi-resolution image fusion," IEEE Transactions on Image Processing, vol. 29, pp. 4980-4995, 2020.

T.Bruylants,P. Schelkens,andA. Tzannes,"JP3D-Extensionsforthree-dimensional data (part 10)," in The JPEG 2000 Suite. Wiley-Blackwell, 2009, pp. 199-227.

T.Bruylants,A. Munteanu,andP.Schelkens,"Waveletbasedvolumetric medical image compression," Signal processing: Image communication, vol. 31, pp. 112-133, 2015.

L. F. Lucas, N. M. Rodrigues, L. A. da Silva Cruz, and S. M. de Faria, "Lossless compression of medical images using 3-D predictors," IEEE Transactions on Medical Imaging, vol. 36, No. 11, pp. 2250-2260, 2017.

D. Spelic and B. Zalik, "Lossless compression of threshold-segmented medical images," Journal of Medical Systems, vol. 36, pp. 2349-2357, 2012.

S. S. Parikh, D. Ruiz, H. Kalva, G. Fernandez-Escribano, and V. Adzic, "High bit-depth medical image compression with Hevc," IEEE Journal of Biomedical and Health Informatics, vol. 22, No. 2, pp. 552-560, 2017.

A. F. Guarda, J. M. Santos, L. A. da Silva Cruz, P. A. Assunc ,ã o, N. M. Rodrigues, and S. M. de Faria, "A method to improve HEVC lossless coding of volumetric medical images," Signal Processing: Image Communication, vol. 59, pp. 96-104, 2017.

V.Sanchez,R.Abugharbieh,andP.Nasiopoulos,"Symmetry-based scalable lossless compression of 3D medical image data," IEEE Transactions on Medical Imaging, vol. 28, No. 7, pp. 1062-1072, 2009.

M. J. Weinberger, G. Seroussi, and G. Sapiro, "The LOCO-I lossless image compression algorithm: Principles and standardization into JPEG-LS," IEEE Transactions on Image Processing, vol. 9, No. 8, pp. 1309-1324, 2000.

A. Skodras, C. Christopoulos, and T. Ebrahimi, "The JPEG 2000 still image compression standard," IEEE Signal Processing Magazine, vol. 18, No. 5, pp. 36-58, 2001.

F. Dufaux, G. J. Sullivan, and T. Ebrahimi, "The JPEG XR image coding standard," IEEE Signal Processing Magazine, vol. 26, No. 6, pp. 195-204, 2009.

J.Alakuijala,R.VanAsseldonk,S. Boukortt,M.Bruse,I.-M.Coms,a, M. Firsching, T. Fischbacher, E. Kliuchnikov, S. Gomez, R. Obryk et al., "JPEG-XL: Next-generation image compression architecture and coding tools," in Proceedings of the Applications of Digital Image Processing XLII, 2019, pp. 112-124.

G. J. Sullivan, J.-R. Ohm, W.-J. Han, and T. Wiegand, "Overview of the high efficiency video coding (HEVC) standard," IEEE Transactions on Circuits and Systems for Video Technology, vol. 22, No. 12, pp. 1649-1668, 2012.

B. Bross, Y.-K. Wang, Y. Ye, S. Liu, J. Chen, G. J. Sullivan, and J.-R. Ohm, "Overview of the versatile video coding (VVC) standard and its applications," IEEE Transactions on Circuits and Systems for Video Technology, vol. 31, No. 10, pp. 3736-3764, 2021.

F. Mentzer, E. Agustsson, M. Tschannen, R. Timofte, and L. V. Gool, "Practical full resolution learned lossless image compression," in Pro-ceedings of the IEEE/CVF Conference on Computer Vision and Pattern Recognition, 2019, pp. 10 629-10 638.

I. Schiopu and A. Munteanu, "Deep-learning-based lossless image cod-ing," IEEE Transactions on Circuits and Systems for Video Technology, vol. 30, No. 7, pp. 1829-1842, 2019.

F. Mentzer, L. V. Gool, and M. Tschannen, "Learning better lossless compression using lossy compression," in Proceedings of the IEEE/CVF Conference on Computer Vision and Pattern Recognition, 2020, pp. 6638-6647.

H.Ma,D.Liu,N. Yan,H. Li,andF.Wu, "End-to-end optimized versatile image compression with wavelet-like transform," IEEE Transactions on Pattern Analysis and Machine Intelligence, vol. 44, No. 3, pp. 1247-1263, 2020.

Y. Bai, X. Liu, W. Zuo, Y. Wang, and X. Ji, "Learning scalable |∞—constrained near-lossless image compression via joint lossy image and residual compression," in Proceedings of the IEEE/CVF Conference on Computer Vision and Pattern Recognition, 2021, pp. 11 946-11 955.

N. Kang, S. Qiu, S. Zhang, Z. Li, and S.-T. Xia, "PILC: Practical image lossless compression with an end-to-end gpu oriented neural framework," in Proceedings of the IEEE/CVF Conference on Computer Vision and Pattern Recognition, 2022, pp. 3739-3748.

S. Zhang, C. Zhang, N. Kang, and Z. Li, "ivpf: Numerical invertible volume preserving flow for efficient lossless compression," in Proceed-ings of the IEEE/CVF Conference on Computer Vision and Pattern Recognition, 2021, pp. 620-629.

(56)                References Cited

OTHER PUBLICATIONS

E. Hoogeboom, J. Peters, R. Van Den Berg, and M. Welling, "Integer discrete flows and lossless compression," in Proceedings of the Advances in Neural Information Processing Systems, 2019, pp. 1-11.

Z.Chen,S.Gu,G.Lu,andD.Xu, "Exploiting Intra-slice and Inter-slice redundancy for learning-based lossless volumetric image compression," IEEE Transactions on Image Processing, vol. 31, pp. 1697-1707, 2022.

D. Xue, H. Ma, L. Li, D. Liu, and Z. Xiong, "aiWave: Volumetric image compression with 3-D trained affine wavelet-like transform," IEEE Transactions on Medical Imaging, vol. 42, No. 3, pp. 606-618, 2022.

N.Bien,P.Rajpurkar,R.L.Ball,J.Irvin,A.Park,E. Jones,M.Bereket, B. N. Patel, K. W. Yeom, K. Shpanskaya et al., "Deep-learning-assisted diagnosis for knee magnetic resonance imaging: Development and retrospective validation of MRNet," PLoS Medicine, vol. 15, No. 11, pp. 1-19, 2018.

J. Sneyers and P. Wuille, "FLIF: Free lossless image format based on Maniac compression," in Proceedings of the IEEE International Conference on Image Processing, 2016, pp. 66-70.

D. S. Taubman and M. W. Marcellin, "JPEG2000: Standard for interactive imaging," Proceedings of the IEEE, vol. 90, No. 8, pp. 1336-1357, 2002.

D. Taubman, "High performance scalable image compression with EBCOT," IEEE Transactions on Image Processing, vol. 9, No. 7, pp. 1158-1170, 2000.

Z.Pan,W.Yu,J.Lei,N. Ling,andS.Kwong, "TSAN: Synthesized view quality enhancement via two-stream attention network for 3D-HEVC," IEEE Transactions on Circuits and Systems for Video Technology, vol. 32, No. 1, pp. 345-358, 2021.

H.Liu,Y.Zhang,H.Zhang,C.Fan,S. Kwong,C.-C.J.Kuo,andX. Fan, "Deep learning-based picture-wise just noticeable distortion prediction model for image compression," IEEE Transactions on Image Processing, vol. 29, pp. 641-656, 2019.

X. Liu, Y. Zhang, S. Hu, S. Kwong, C.-C. J. Kuo, and Q. Peng, "Subjective and objective video quality assessment of 3D synthesized views with texture/depth compression distortion," IEEE Transactions on Image Processing, vol. 24, No. 12, pp. 4847-4861, 2015.

Z. Ni, W. Yang, S. Wang, L. Ma, and S. Kwong, "Towards unsupervised deep image enhancement with generative adversarial network," IEEE Transactions on Image Processing, vol. 29, pp. 9140-9151, 2020.

H. Yuan, S. Kwong, J. Liu, and J. Sun, "A novel distortion model and lagrangian multiplier for depth maps coding," IEEE Transactions on Circuits and Systems for Video Technology, vol. 24, No. 3, pp. 443-451, 2013.

G. Lu, W. Ouyang, D. Xu, X. Zhang, C. Cai, and Z. Gao, "DVC: An end-to-end deep video compression framework," in Proceedings of the IEEE/CVF Conference on Computer Vision and Pattern Recognition, 2019, pp. 11 006-11 015.

Z. Hu, G. Lu, and D. Xu, "FVC: A new framework towards deep video compression in feature space," in Proceedings of the IEEE/ CVF Conference on Computer Vision and Pattern Recognition, 2021, pp. 1502-1511.

J. Li, B. Li, and Y. Lu, "Deep contextual video compression," in Proceedings of the Advances in Neural Information Processing Systems, 2021, pp. 18 114-18 125.

A. Djelouah, J. Campos, S. Schaub-Meyer, and C. Schroers, "Neural inter-frame compression for video coding," in Proceedings of the IEEE/CVF international conference on computer vision, 2019, pp. 6421-6429.

Z. Chen, G. Lu, Z. Hu, S. Liu, W. Jiang, and D. Xu, "LSVC: A learning-based stereo video compression framework," in Proceedings of the IEEE/CVF Conference on Computer Vision and Pattern Recognition, 2022, pp. 6073-6082.

D. Alexandre, H.-M. Hang, and W.-H. Peng, "Hierarchical B-frame video coding using two-layer canf without motion coding," in Pro-ceedings of the IEEE/CVF Conference on Computer Vision and Pattern Recognition, 2023, pp. 10 249-10 258.

M. A. Yilmaz and A. M. Tekalp, "End-to-end rate-distortion opti-mized learned hierarchical bi-directional video compression," IEEE Transac-tions on Image Processing, vol. 31, pp. 974-983, 2021.

H. Liu, M. Lu, Z. Ma, F. Wang, Z. Xie, X. Cao, and Y. Wang, "Neural video coding using multiscale motion compensation and spatiotemporal context model," IEEE Transactions on Circuits and Systems for Video Technology, vol. 31, No. 8, pp. 3182-3196, 2020.

H.Liu,M.Lu,Z.Chen,X.Cao,Z.Ma,andY.Wang, "End-to-endneural video coding using a compound spatiotemporal representation," IEEE Transactions on Circuits and Systems for Video Technology, vol. 32, No. 8, pp. 5650-5662, 2022.

Z. Hu, Z. Chen, D. Xu, G. Lu, W. Ouyang, and S. Gu, "Improving deep video compression by resolution-adaptive flow coding," in Proceedings of the European Conference on Computer Vision, 2020, pp. 193-209.

D. Jin, J. Lei, B. Peng, Z. Pan, L. Li, and N. Ling, "Learned video com-pression with efficient temporal context learning," IEEE Trans-actions on Image Processing, 2023, early access.

J. Li, B. Li, and Y. Lu, "Neural video compression with diverse contexts," in Proceedings of the IEEE/CVF Conference on Com-puter Vision and Pattern Recognition, 2023, pp. 22 616-22 626.

L.Qi,J.Li,B.Li,H.Li,andY.Lu, "Motion information propagation for neural video compression," in Proceedings of the IEEE/CVF Con-ference on Computer Vision and Pattern Recognition, 2023, pp. 6111-6120.

F. Mentzer, G. D. Toderici, D. Minnen, S. Caelles, S. J. Hwang, M. Lucic, and E. Agustsson, "VCT: A video compression Transformer," in Proceedings of the Advances in Neural Information Processing Systems, 2022, pp. 13 091-13 103.

J. Xiang, K. Tian, and J. Zhang, "MIMT: Masked image modeling Transformer for video compression," in Proceedings of the Inter-national Conference on Learning Representations, 2022, pp. 1-12.

Z. Chen, L. Relic, R. Azevedo, Y. Zhang, M. Gross, D. Xu, L. Zhou, and C. Schroers, "Neural video compression with spatio-temporal cross-covariance Transformers," in Proceedings of the ACM Inter-national Conference on Multimedia, 2023, pp. 8543-8551.

J. Li, B. Li, and Y. Lu, "Hybrid spatial-temporal entropy modelling for neural video compression," in Proceedings of the ACM Inter-national Conference on Multimedia, 2022, pp. 1503-1511.

B. Liu, Y. Chen, R. C. Machineni, S. Liu, and H.-S. Kim, "MMVC: Learned multi-mode video compression with block-based predic-tion mode selection and density-adaptive entropy coding," in Pro-ceedings of the IEEE/CVF Conference on Computer Vision and Pattern Recognition, 2023, pp. 18 487-18 496.

H. Guo, S. Kwong, D. Ye, and S. Wang, "Enhanced context mining and filtering for learned video compression," IEEE Transactions on Multimedia, 2023.

H. Schwarz, D. Marpe, and T. Wiegand, "Analysis of hierarchical B pictures and MCTF," in Proceedings of the IEEE International Conference on Multimedia and Expo, 2006, pp. 1929-1932.

C. E. Shannon, "A mathematical theory of communication," The Bell System Technical Journal, vol. 27, No. 3, pp. 379-423, 1948.

J. Blackburn and M. N. Do, "Two-dimensional geometric lifting," in Proceedings of the IEEE International Conference on Image Processing, 2009, pp. 3817-3820.

A. Moffat, R. M. Neal, and I. H. Witten, "Arithmetic coding revisited," ACM Transactions on Information Systems, vol. 16, No. 3, pp. 256-294, 1998.

T. Fechter and D. Baltas, "One-shot learning for deformable medi-cal image registration and periodic motion tracking," IEEE Trans-actions on Medical Imaging, vol. 39, No. 7, pp. 2506-2517, 2020.

K. S. 2019. Mader, "TRABIT2019 imaging biomarkers," [Online]. Available: https://kaggle.com/competitions/trabit2019-imaging-biomarkers.

S. P. Morozov, A. Andreychenko, N. Pavlov, A. Vladzymyrskyy, N. Ledikhova, V. Gombolevskiy, I. A. Blokhin, P. Gelezhe, A. Gonchar, and V. Y. Chernina, "MosMedData: Chest CT scans with COVID-19 related findings dataset," arXiv preprint arXiv:2005.06465, pp. 1-4, 2020.

M. Jaderberg, K. Simonyan, A. Zisserman et al., "Spatial trans-former networks," in Proceedings of the Advances in Neural Infor-mation Processing Systems, 2015, pp. 1-10.

(56) References Cited

OTHER PUBLICATIONS

A. Dosovitskiy, L. Beyer, A. Kolesnikov, D. Weissenborn, X. Zhai, T. Unterthiner, M. Dehghani, M. Minderer, G. Heigold, S. Gelly et al., "An image is worth 16×16 words: Transformers for image recognition at scale," in Proceedings of the International Conference on Learning Representations, 2021, pp. 1-12.
Z. Huang, X. Wang, Y. Wei, L. Huang, H. Shi, W. Liu, and T. S. Huang, "CCNet: Criss-cross attention for semantic segmentation," IEEE Transactions on Pattern Analysis and Machine Intelligence, vol. 45, No. 6, pp. 6896-6908, 2023.
K. He, X. Zhang, S. Ren, and J. Sun, "Deep residual learning for image recognition," in Proceedings of the IEEE conference on computer vision and pattern recognition, 2016, pp. 770-778.
A. Paszke, S. Gross, F. Massa, A. Lerer, J. Bradbury, G. Chanan, T. Killeen, Z. Lin, N. Gimelshein, L. Antiga et al., "PyTorch: An imperative style, high-performance deep learning library," in Proceedings of the Advances in Neural Information Processing Systems, 2019.
M. Larobina and L. Murino, "Medical image file formats," Journal of digital imaging, vol. 27, pp. 200-206, 2014.

D. Xue, L. Li, and D. Liu, "An end-to-end 3D biomedical image coding scheme based on learning wavelet transform," AVS Document, M7700, 2023.
G. Roelofs, PNG: The definitive guide. O'Reilly Media, 1999.
N. Michael, "FFV1 video codec specification," 2013. [Online]. Available: https://www.ffmpeg.org/¤ michael/ffv1.html.
J. Balle , V. Laparra, and E. P. Simoncelli, "End-to-end optimized image compression," in Proceedings of the International Conference on Learning Representations, 2017, pp. 1-12.
A. Wieckowski, J. Brandenburg, T. Hinz, C. Bartnik, V. George, G. Hege, C. Helmrich, A. Henkel, C. Lehmann, C. Stoffers et al., "VVenC: An open and optimized VVC encoder implementation," in Proceedings of the IEEE International Conference on Multimedia & Expo Workshops, 2021, pp. 1-2.
A.Wieckowski,G.Hege,C. Bartnik,C.Lehmann,C. Stoffers,B. Bross, and D. Marpe, "Towards a live software decoder implementation for the upcoming versatile video coding (VVC) codec," in Proceedings of the IEEE International Conference on Image Processing, 2020, pp. 3124-3128.

* cited by examiner

TABLE II

PERFORMANCE COMPARISONS ON THE MRNET DATASET.

| Methods | Axial | | | Coronal | | | Sagittal | | |
|---|---|---|---|---|---|---|---|---|---|
| | Bpp ↓ | Compression Ratio ↑ | Bitrate Saving Ratio ↑ | Bpp ↓ | Compression Ratio ↑ | Bitrate Saving Ratio ↑ | Bpp ↓ | Compression Ratio ↑ | Bitrate Saving Ratio ↑ |
| PNG [ ] | 5.36 | 1.493 | -10.2% | 4.58 | 1.747 | -14.4% | 5.58 | 1.434 | -8.2% |
| JPEG-LS [ ] | 4.91 | 1.629 | -1.0% | 4.07 | 1.966 | -1.8% | 5.24 | 1.527 | -1.5% |
| JPEG-2000 [ ] | 5.02 | 1.594 | -3.2% | 4.17 | 1.918 | -4.3% | 5.31 | 1.507 | -2.9% |
| JP3D [ ] | 4.98 | 1.606 | -2.4% | 4.15 | 1.928 | -3.7% | 5.28 | 1.515 | -2.3% |
| JPEG-2000-Part2 [ ] | 5.00 | 1.600 | -2.9% | 4.16 | 1.923 | -3.9% | 5.30 | 1.509 | -2.6% |
| FLIF [ ] | 4.86 | 1.646 | 0.0% | 4.00 | 2.000 | 0.0% | 5.16 | 1.550 | 0.0% |
| JPEG-XL [ ] | 4.72 | 1.693 | 2.9% | 3.89 | 2.057 | 2.8% | 5.09 | 1.572 | 1.4% |
| HEVC-Intra [ ] | 5.31 | 1.507 | -9.2% | 4.47 | 1.790 | -11.8% | 5.64 | 1.418 | -9.3% |
| HEVC [ ] | 5.19 | 1.541 | -6.8% | 4.47 | 1.790 | -11.7% | 5.58 | 1.434 | -8.1% |
| HEVC-RExt-Intra [ ] | 5.24 | 1.527 | -7.7% | 4.35 | 1.839 | -8.7% | 5.63 | 1.421 | -9.1% |
| HEVC-RExt [ ] | 5.11 | 1.566 | -5.1% | 4.20 | 1.905 | -5.1% | 5.50 | 1.455 | -6.6% |
| FFV1 [ ] | 4.86 | 1.646 | 0.0% | 4.03 | 1.985 | -0.7% | 5.19 | 1.541 | -0.5% |
| VVC-Intra [ ] | 4.99 | 1.603 | -2.7% | 4.11 | 1.946 | -2.8% | 5.33 | 1.501 | -3.3% |
| VVC [ ] | 4.96 | 1.613 | -2.1% | 4.10 | 1.951 | -2.5% | 5.32 | 1.503 | -3.1% |
| L3C [ ] | 5.16 | 1.550 | -6.2% | 4.45 | 1.798 | -11.3% | 5.52 | 1.449 | -7.0% |
| ICEC [ ] | 4.64 | 1.724 | 4.5% | 3.84 | 2.083 | 4.0% | 4.97 | 1.610 | 3.6% |
| aiWave [ ] | 4.55 | 1.758 | 6.5% | 3.80 | 2.105 | 4.9% | 4.83 | 1.656 | 6.4% |
| Proposed | 4.41 | 1.814 | 9.2% | 3.63 | 2.204 | 9.3% | 4.81 | 1.663 | 6.9% |

Fig. 11

SYSTEM AND METHOD FOR COMPRESSING AND/OR RECONSTRUCTING MEDICAL IMAGE

FIELD OF INVENTION

This invention generally relates to system and method for processing a medical image, and in particular, to system and method for compressing and/or reconstructing a medical image.

BACKGROUND OF INVENTION

With the advancement of medical image acquisition and processing technologies, 3D (three-dimensional) medical images, such as magnetic resonance imaging (MRI) and computer tomography (CT), have become increasingly prevalent in medical diagnosis [1]-[5] and disease treatment [6]-[8]. Compared with 2D (two-dimensional) images, 3D medical images used in diagnosis applications suffer from dramatically increased data volume. Therefore, it is crucial and imperative to develop efficient lossless compression techniques for 3D medical images.

Traditional lossless 3D medical image compression methods can be categorized into two types: 3D transform-based methods [9]-[12] and sequence-based methods [13]-[15]. Methods in the first class implement 3D transforms, such as 3D discrete cosine transform (DCT) and 3D discrete wavelet transform (DWT), to transform input 3D medical images to 3D coefficients. The coefficients are then compressed to bitstreams with entropy coding. On the other hand, sequence-based methods rely on off-the-shelf lossless 2D compression techniques [16]-[21] to sequentially encode slices of input 3D images, in which intra and inter predictions are performed to reduce redundancies. Although traditional methods have showcased effectiveness in 3D medical image compression, they rely heavily on hand-crafted components for redundancy reduction, limiting their adaptability to the specific characteristics of 3D medical images and consequently impeding further advancements.

The rise of deep learning techniques has prompted a surge of research on deep lossless 2D image compression, as evidenced by the growing number of works in this area [22]-[29]. Despite the fact that such end-to-end trained codec can be applied to each slice of 3D medical images individually, there remains a pressing need for a mechanism capable of reducing inter-slice redundancy in 3D medical images. To address this issue, researchers have preliminarily studied deep lossless compression for 3D medical images and proposed several methods that leverage the characteristics of 3D medical images [30], [31]. In particular, the sequence-based method [30] benefits from the reference-based inter-coding philosophy that contexts extracted from the current slice (e.g., hyper-priors) and reference slice (e.g., latent features) are jointly utilized as conditional priors for probability estimation in entropy encoding. Though promising performance has been achieved, the inherent characteristics of 3D medical images, i.e., the bilateral correlations, have not been exploited in the generation of contextual priors.

REFERENCES

The following references are referred to throughout this specification, as indicated by the numbered brackets, each of the references being entirely incorporated herein by reference.

[1] P. Rajpurkar, E. Chen, O. Banerjee, and E. J. Topol, "AI in health and medicine," Nature Medicine, vol. 28, no. 1, pp. 31-38, 2022.

[2] Z. Zheng, J. S. Lauritzen, E. Perlman, C. G. Robinson, M. Nichols, D. Milkie, O. Torrens, J. Price, C. B. Fisher, N. Sharifi et al., "A complete electron microscopy volume of the brain of adult Drosophila melanogaster," Cell, vol. 174, no. 3, pp. 730-743, 2018.

[3] Y. Zhang, Y. Wei, Q. Wu, P. Zhao, S. Niu, J. Huang, and M. Tan, "Collaborative unsupervised domain adaptation for medical image diagnosis," IEEE Transactions on Image Processing, vol. 29, pp. 7834-7844, 2020.

[4] S. Zhou, D. Nie, E. Adeli, J. Yin, J. Lian, and D. Shen, "High-resolution encoder-decoder networks for low-contrast medical image segmentation," IEEE Transactions on Image Processing, vol. 29, pp. 461-475, 2019.

[5] W. Tang, F. He, Y. Liu, and Y. Duan, "MATR: Multimodal medical image fusion via multiscale adaptive transformer," IEEE Transactions on Image Processing, vol. 31, pp. 5134-5149, 2022.

[6] D. Zhang, G. Huang, Q. Zhang, J. Han, J. Han, Y. Wang, and Y. Yu, "Exploring task structure for brain tumor segmentation from multi-modality MR images," IEEE Transactions on Image Processing, vol. 29, pp. 9032-9043, 2020.

[7] A. Esteva, A. Robicquet, B. Ramsundar, V. Kuleshov, M. DePristo, K. Chou, C. Cui, G. Corrado, S. Thrun, and J. Dean, "A guide to deep learning in healthcare," Nature Medicine, vol. 25, no. 1, pp. 24-29, 2019.

[8] J. Ma, H. Xu, J. Jiang, X. Mei, and X.-P. Zhang, "DDcGAN: A dual-discriminator conditional generative adversarial network for multi-resolution image fusion," IEEE Transactions on Image Processing, vol. 29, pp. 4980-4995, 2020.

[9] T. Bruylants, P. Schelkens, and A. Tzannes, "JP3D-Extensions for three-dimensional data (part 10)," in The JPEG 2000 Suite. Wiley-Blackwell, 2009, pp. 199-227.

[10] T. Bruylants, A. Munteanu, and P. Schelkens, "Wavelet based volumetric medical image compression," Signal processing: Image communication, vol. 31, pp. 112-133, 2015.

[11] L. F. Lucas, N. M. Rodrigues, L. A. da Silva Cruz, and S. M. de Faria, "Lossless compression of medical images using 3-D predictors," IEEE Transactions on Medical Imaging, vol. 36, no. 11, pp. 2250-2260, 2017.

[12] D. Spelič and B. Zalik, "Lossless compression of threshold-segmented medical images," Journal of Medical Systems, vol. 36, pp. 2349-2357, 2012.

[13] S. S. Parikh, D. Ruiz, H. Kalva, G. Fernandez-Escribano, and V. Adzic, "High bit-depth medical image compression with HEVC," IEEE Journal of Biomedical and Health Informatics, vol. 22, no. 2, pp. 552-560, 2017.

[14] A. F. Guarda, J. M. Santos, L. A. da Silva Cruz, P. A. Assungio, N. M. Rodrigues, and S. M. de Faria, "A method to improve HEVC lossless coding of volumetric medical images," Signal Processing: Image Communication, vol. 59, pp. 96-104, 2017.

[15] V. Sanchez, R. Abugharbieh, and P. Nasiopoulos, "Symmetry-based scalable lossless compression of 3D medical image data," IEEE Transactions on Medical Imaging, vol. 28, no. 7, pp. 1062-1072, 2009.

[16] M. J. Weinberger, G. Seroussi, and G. Sapiro, "The LOCO-I lossless image compression algorithm: Principles and standardization into JPEG-LS," IEEE Transactions on Image Processing, vol. 9, no. 8, pp. 1309-1324, 2000.

[17] A. Skodras, C. Christopoulos, and T. Ebrahimi, "The JPEG 2000 still image compression standard," IEEE Signal Processing Magazine, vol. 18, no. 5, pp. 36-58, 2001.

[18] F. Dufaux, G. J. Sullivan, and T. Ebrahimi, "The JPEG XR image coding standard," IEEE Signal Processing Magazine, vol. 26, no. 6, pp. 195-204, 2009.

[19] J. Alakuijala, R. Van Asseldonk, S. Boukortt, M. Bruse, I.-M. Comsa, M. Firsching, T. Fischbacher, E. Kliuchnikov, S. Gomez, R. Obryk et al., "JPEG-XL: Next-generation image compression architecture and coding tools," in Proceedings of the Applications of Digital Image Processing XLII, 2019, pp. 112-124.

[20] G. J. Sullivan, J.-R. Ohm, W.-J. Han, and T. Wiegand, "Overview of the high efficiency video coding (HEVC) standard," IEEE Transactions on Circuits and Systems for Video Technology, vol. 22, no. 12, pp. 1649-1668, 2012.

[21] B. Bross, Y.-K. Wang, Y. Ye, S. Liu, J. Chen, G. J. Sullivan, and J.-R. Ohm, "Overview of the versatile video coding (VVC) standard and its applications," IEEE Transactions on Circuits and Systems for Video Technology, vol. 31, no. 10, pp. 3736-3764, 2021.

[22] F. Mentzer, E. Agustsson, M. Tschannen, R. Timofte, and L. V. Gool, "Practical full resolution learned lossless image compression," in Proceedings of the IEEE/CVF Conference on Computer Vision and Pattern Recognition, 2019, pp. 10 629-10 638.

[23] I. Schiopu and A. Munteanu, "Deep-learning-based lossless image coding," IEEE Transactions on Circuits and Systems for Video Technology, vol. 30, no. 7, pp. 1829-1842, 2019.

[24] F. Mentzer, L. V. Gool, and M. Tschannen, "Learning better lossless compression using lossy compression," in Proceedings of the IEEE/CVF Conference on Computer Vision and Pattern Recognition, 2020, pp. 6638-6647.

[25] H. Ma, D. Liu, N. Yan, H. Li, and F. Wu, "End-to-end optimized versatile image compression with wavelet-like transform," IEEE Transactions on Pattern Analysis and Machine Intelligence, vol. 44, no. 3, pp. 1247-1263, 2020.

[26] Y. Bai, X. Liu, W. Zuo, Y. Wang, and X. Ji, "Learning scalable $l^\infty$-constrained near-lossless image compression via joint lossy image and residual compression," in Proceedings of the IEEE/CVF Conference on Computer Vision and Pattern Recognition, 2021, pp. 11 946-11 955.

[27] N. Kang, S. Qiu, S. Zhang, Z. Li, and S.-T. Xia, "PILC: Practical image lossless compression with an end-to-end gpu oriented neural framework," in Proceedings of the IEEE/CVF Conference on Computer Vision and Pattern Recognition, 2022, pp. 3739-3748.

[28] S. Zhang, C. Zhang, N. Kang, and Z. Li, "ivpf: Numerical invertible volume preserving flow for efficient lossless compression," in Proceedings of the IEEE/CVF Conference on Computer Vision and Pattern Recognition, 2021, pp. 620-629.

[29] E. Hoogeboom, J. Peters, R. Van Den Berg, and M. Welling, "Integer discrete flows and lossless compression," in Proceedings of the Advances in Neural Information Processing Systems, 2019, pp. 1-11.

[30] Z. Chen, S. Gu, G. Lu, and D. Xu, "Exploiting intra-slice and inter-slice redundancy for learning-based lossless volumetric image compression," IEEE Transactions on Image Processing, vol. 31, pp. 1697-1707, 2022.

[31] D. Xue, H. Ma, L. Li, D. Liu, and Z. Xiong, "ai Wave: Volumetric image compression with 3-D trained affine wavelet-like transform," IEEE Transactions on Medical Imaging, vol. 42, no. 3, pp. 606-618, 2022.

[32] N. Bien, P. Rajpurkar, R. L. Ball, J. Irvin, A. Park, E. Jones, M. Bereket, B. N. Patel, K. W. Yeom, K. Shpanskaya et al., "Deep-learning-assisted diagnosis for knee magnetic resonance imaging: Development and retrospective validation of MR Net," PLoS Medicine, vol. 15, no. 11, pp. 1-19, 2018.

[33] J. Sneyers and P. Wuille, "FLIF: Free lossless image format based on MANIAC compression," in Proceedings of the IEEE International Conference on Image Processing, 2016, pp. 66-70.

[34] D. S. Taubman and M. W. Marcellin, "JPEG2000: Standard for interactive imaging," Proceedings of the IEEE, vol. 90, no. 8, pp. 1336-1357, 2002.

[35] D. Taubman, "High performance scalable image compression with EBCOT," IEEE Transactions on Image Processing, vol. 9, no. 7, pp. 1158-1170, 2000.

[36] Z. Pan, W. Yu, J. Lei, N. Ling, and S. Kwong, "TSAN: Synthesized view quality enhancement via two-stream attention network for 3D-HEVC," IEEE Transactions on Circuits and Systems for Video Technology, vol. 32, no. 1, pp. 345-358, 2021.

[37] H. Liu, Y. Zhang, H. Zhang, C. Fan, S. Kwong, C.-C. J. Kuo, and X. Fan, "Deep learning-based picture-wise just noticeable distortion prediction model for image compression," IEEE Transactions on Image Processing, vol. 29, pp. 641-656, 2019.

[38] X. Liu, Y. Zhang, S. Hu, S. Kwong, C.-C. J. Kuo, and Q. Peng, "Subjective and objective video quality assessment of 3D synthesized views with texture/depth compression distortion," IEEE Transactions on Image Processing, vol. 24, no. 12, pp. 4847-4861, 2015.

[39] Z. Ni, W. Yang, S. Wang, L. Ma, and S. Kwong, "Towards unsupervised deep image enhancement with generative adversarial network," IEEE Transactions on Image Processing, vol. 29, pp. 9140-9151, 2020.

[40] H. Yuan, S. Kwong, J. Liu, and J. Sun, "A novel distortion model and lagrangian multiplier for depth maps coding," IEEE Transactions on Circuits and Systems for Video Technology, vol. 24, no. 3, pp. 443-451, 2013.

[41] G. Lu, W. Ouyang, D. Xu, X. Zhang, C. Cai, and Z. Gao, "DVC: An end-to-end deep video compression framework," in Proceedings of the IEEE/CVF Conference on Computer Vision and Pattern Recognition, 2019, pp. 11 006-11 015.

[42] Z. Hu, G. Lu, and D. Xu, "FVC: A new framework towards deep video compression in feature space," in Proceedings of the IEEE/CVF Conference on Computer Vision and Pattern Recognition, 2021, pp. 1502-1511.

[43] J. Li, B. Li, and Y. Lu, "Deep contextual video compression," in Proceedings of the Advances in Neural Information Processing Systems, 2021, pp. 18 114-18 125.

[44] A. Djelouah, J. Campos, S. Schaub-Meyer, and C. Schroers, "Neural inter-frame compression for video coding," in Proceedings of the IEEE/CVF international conference on computer vision, 2019, pp. 6421-6429.

[45] Z. Chen, G. Lu, Z. Hu, S. Liu, W. Jiang, and D. Xu, "LSVC: A learning-based stereo video compression framework," in Proceedings of the IEEE/CVF Conference on Computer Vision and Pattern Recognition, 2022, pp. 6073-6082.

[46] D. Alexandre, H.-M. Hang, and W.-H. Peng, "Hierarchical B-frame video coding using two-layer canf without motion coding," in Proceedings of the IEEE/CVF Conference on Computer Vision and Pattern Recognition, 2023, pp. 10 249-10 258.

[47] M. A. Yilmaz and A. M. Tekalp, "End-to-end rate-distortion optimized learned hierarchical bi-directional video compression," IEEE Transactions on Image Processing, vol. 31, pp. 974-983, 2021.

[48] H. Liu, M. Lu, Z. Ma, F. Wang, Z. Xie, X. Cao, and Y. Wang, "Neural video coding using multiscale motion compensation and spatiotemporal context model," IEEE Transactions on Circuits and Systems for Video Technology, vol. 31, no. 8, pp. 3182-3196, 2020.

[49] H. Liu, M. Lu, Z. Chen, X. Cao, Z. Ma, and Y. Wang, "End-to-end neural video coding using a compound spatiotemporal representation," IEEE Transactions on Circuits and Systems for Video Technology, vol. 32, no. 8, pp. 5650-5662, 2022.

[50] Z. Hu, Z. Chen, D. Xu, G. Lu, W. Ouyang, and S. Gu, "Improving deep video compression by resolution-adaptive flow coding," in Proceedings of the European Conference on Computer Vision, 2020, pp. 193-209.

[51] D. Jin, J. Lei, B. Peng, Z. Pan, L. Li, and N. Ling, "Learned video com-pression with efficient temporal context learning," IEEE Transactions on Image Processing, 2023, early access.

[52] J. Li, B. Li, and Y. Lu, "Neural video compression with diverse contexts," in Proceedings of the IEEE/CVF Conference on Computer Vision and Pattern Recognition, 2023, pp. 22 616-22 626.

[53] L. Qi, J. Li, B. Li, H. Li, and Y. Lu, "Motion information propagation for neural video compression," in Proceedings of the IEEE/CVF Conference on Computer Vision and Pattern Recognition, 2023, pp. 6111-6120.

[54] F. Mentzer, G. D. Toderici, D. Minnen, S. Caelles, S. J. Hwang, M. Lucic, and E. Agustsson, "VCT: A video compression Transformer," in Proceedings of the Advances in Neural Information Processing Systems, 2022, pp. 13 091-13 103.

[55] J. Xiang, K. Tian, and J. Zhang, "MIMT: Masked image modeling Transformer for video compression," in Proceedings of the International Conference on Learning Representations, 2022, pp. 1-12.

[56] Z. Chen, L. Relic, R. Azevedo, Y. Zhang, M. Gross, D. Xu, L. Zhou, and C. Schroers, "Neural video compression with spatiotemporal cross-covariance Transformers," in Proceedings of the ACM International Conference on Multimedia, 2023, pp. 8543-8551.

[57] J. Li, B. Li, and Y. Lu, "Hybrid spatial-temporal entropy modelling for neural video compression," in Proceedings of the ACM International Conference on Multimedia, 2022, pp. 1503-1511.

[58] B. Liu, Y. Chen, R. C. Machineni, S. Liu, and H.-S. Kim, "MMVC: Learned multi-mode video compression with block-based prediction mode selection and density-adaptive entropy coding," in Proceedings of the IEEE/CVF Conference on Computer Vision and Pattern Recognition, 2023, pp. 18 487-18 496.

[59] H. Guo, S. Kwong, D. Ye, and S. Wang, "Enhanced context mining and filtering for learned video compression," IEEE Transactions on Multimedia, 2023.

[60] H. Schwarz, D. Marpe, and T. Wiegand, "Analysis of hierarchical B pictures and MCTF," in Proceedings of the IEEE International Conference on Multimedia and Expo, 2006, pp. 1929-1932.

[61] C. E. Shannon, "A mathematical theory of communication," The Bell System Technical Journal, vol. 27, no. 3, pp. 379-423, 1948.

[62] J. Blackburn and M. N. Do, "Two-dimensional geometric lifting," in Proceedings of the IEEE International Conference on Image Processing, 2009, pp. 3817-3820.

[63] A. Moffat, R. M. Neal, and I. H. Witten, "Arithmetic coding revisited," ACM Transactions on Information Systems, vol. 16, no. 3, pp. 256-294, 1998.

[64] T. Fechter and D. Baltas, "One-shot learning for deformable medical image registration and periodic motion tracking," IEEE Transactions on Medical Imaging, vol. 39, no.7, pp. 2506-2517, 2020.

[65] K. S. 2019. Mader, "TRABIT2019 imaging biomarkers," [Online]. Available: https://kaggle.com/competitions/trabit2019-imaging-biomarkers

[66] S. P. Morozov, A. Andreychenko, N. Pavlov, A. Vladzymyrskyy, N. Ledikhova, V. Gombolevskiy, I. A. Blokhin, P. Gelezhe, A. Gonchar, and V. Y. Chernina, "MosMedData: Chest CT scans with COVID-19 related findings dataset," arXiv preprint arXiv:2005.06465, pp. 1-4, 2020.

[67] M. Jaderberg, K. Simonyan, A. Zisserman et al., "Spatial transformer networks," in Proceedings of the Advances in Neural Information Processing Systems, 2015, pp. 1-10.

[68] A. Dosovitskiy, L. Beyer, A. Kolesnikov, D. Weissenborn, X. Zhai, T. Unterthiner, M. Dehghani, M. Minderer, G. Heigold, S. Gelly et al., "An image is worth 16×16 words: Transformers for image recognition at scale," in Proceedings of the International Conference on Learning Representations, 2021, pp. 1-12.

[69] Z. Huang, X. Wang, Y. Wei, L. Huang, H. Shi, W. Liu, and T. S. Huang, "CCNet: Criss-cross attention for semantic segmentation," IEEE Transactions on Pattern Analysis and Machine Intelligence, vol. 45, no. 6, pp. 6896-6908, 2023.

[70] K. He, X. Zhang, S. Ren, and J. Sun, "Deep residual learning for image recognition," in Proceedings of the IEEE conference on computer vision and pattern recognition, 2016, pp. 770-778.

[71] A. Paszke, S. Gross, F. Massa, A. Lerer, J. Bradbury, G. Chanan, T. Killeen, Z. Lin, N. Gimelshein, L. Antiga et al., "PyTorch: An imperative style, high-performance deep learning library," in Proceedings of the Advances in Neural Information Processing Systems, 2019.

[72] M. Larobina and L. Murino, "Medical image file formats," Journal of digital imaging, vol. 27, pp. 200-206, 2014.

[73] D. Xue, L. Li, and D. Liu, "An end-to-end 3D biomedical image coding scheme based on learning wavelet transform," AVS Document, M7700, 2023.

[74] G. Roelofs, PNG: The definitive guide. O'Reilly Media, 1999.

[75] N. Michael, "FFV1 video codec specification," 2013. [Online]. Available: https://www.ffmpeg.org/-michael/ffv1.html

[76] J. Balle, V. Laparra, and E. P. Simoncelli, "End-to-end optimized image compression," in Proceedings of the International Conference onLearning Representations, 2017, pp. 1-12.

[77] A. Wieckowski, J. Brandenburg, T. Hinz, C. Bartnik, V. George, G. Hege, C. Helmrich, A. Henkel, C. Lehmann, C. Stoffers et al., "VVenC: An open and optimized VVC encoder implementation," in Proceedings of the IEEE International Conference on Multimedia & Expo Workshops, 2021, pp. 1-2.

[78] A. Wieckowski, G. Hege, C. Bartnik, C. Lehmann, C. Stoffers, B. Bross, and D. Marpe, "Towards a live software decoder implementation for the upcoming versatile video coding (VVC) codec," in Proceedings of the IEEE International Conference on Image Processing, 2020, pp. 3124-3128.

SUMMARY OF INVENTION

Accordingly, the present invention, in a first aspect, is a method for compressing a 3D medical image. The method includes the steps of receiving a 3D medical image, partitioning the 3D medical image into a plurality of first slices, encoding the plurality of the first slices by a lossy codec into first bitstreams, decoding the first bitstreams by the lossy codec to obtain a plurality of second slices, computing a plurality of residues by comparing the plurality of the first slices and the plurality of the second slices, encoding the plurality of the residues by a lossless codec to obtain a plurality of encoded residues, and outputting the first bitstreams and the plurality of the encoded residues as compressed image data. Each residue corresponds to one of the first slices and its corresponding second slice.

In some embodiments, the step of partitioning the 3D medical image further includes partitioning the 3D medical image along an axis general perpendicular to a partition plane.

In some embodiments, the lossy codec is selected from the group consisting Versatile Video Coding (VVC), High Efficiency Video Coding (HEVC), H.264/MPEG-4 AVC, and Audio Video coding Standard (AVS).

In some embodiments, the step of encoding the plurality of the residues is based on intra-slice bilateral contexts and inter-slice bilateral contexts.

In some embodiments, the step of encoding the plurality of the residues further includes obtaining bi-directional references for at least some of the plurality of the residues, and extracting the inter-slice bilateral contexts from the bi-directional references and the plurality of the second slices.

In some embodiments, the step of extracting the inter-slice bilateral contexts from the bi-directional references and the plurality of the second slices, further includes: applying residual blocks to the bi-directional references and the plurality of the second slices to obtain inter-slice features, processing the inter-slice features by a bi-directional cross-attention module to generate inter-slice reference information, and further processing the inter-slice reference information to obtain the inter-slice bilateral contexts.

In some embodiments, the step of further processing the inter-slice reference information to obtain the inter-slice bilateral contexts, includes normalizing and concatenating the inter-slice reference information, and feeding the inter-slice reference information to a feed-forward network to generate the inter-slice bilateral contexts.

In some embodiments, the step of encoding the plurality of the residues further includes extracting intra-slice features from the plurality of the second slices, and processing the intra-slice features by a symmetry-based intra-slice context extraction (SICE) module to generate the intra-slice contexts.

In some embodiments, the step of processing the intra-slice features is conducted by the SICE based on local-symmetric properties of tissues.

In some embodiments, the step of processing the intra-slice features further includes aggregating neighborhood information in the intra-slice features to obtain local symmetry.

In some embodiments, the step of processing the intra-slice features is conducted by the SICE based on inherent anatomical symmetry of a human body.

In some embodiments, the step of processing the intra-slice features further includes obtaining long-range correlations in the intra-slice features to obtain global symmetry.

In some embodiments, the step of outputting the compressed image data further includes merging the first bitstreams and the plurality of the encoded residues into a data file or into data streams.

In some embodiments, the bi-directional references are obtained using a hierarchical-B coding structure.

In some embodiments, the step of encoding the plurality of the residues further includes parametrically modelling probability distributions of each of the plurality of residues based on the inter-slice contexts and the intra-slice contexts, and encoding the plurality of the residues using an arithmetic coding algorithm based on the probability distributions to generate the plurality of encoded residues.

According to a second aspect of the invention, there is provided a method for decompressing compressed image data to obtain a 3D medical image. The method includes the steps of receiving compressed image data, extracting first bitstreams and second bitstreams from the compressed image data, decoding the second bitstreams by a lossless codec to obtain a plurality of residues, decoding the first bitstreams by a lossy codec to obtain a plurality of second slices, adding to the plurality of the residues to the plurality of the second slices to obtain a plurality of first slices, and combining the plurality of the first slices to obtain a 3D medical image. For each of the plurality of the second slices a corresponding of the plurality of the residues is added thereto.

According to a third aspect of the invention, there is provided a system for processing a medical image. The system contains one or more processors, and memory storing one or more programs configured to be executed by the one or more processors, the one or more programs including instructions for performing or facilitating performing the method for compressing a 3D medical image or the method for decompressing compressed image data to obtain a 3D medical image, as mentioned above. The system may further include an input device for receiving user input. The system may further include a display for displaying processed images and data (e.g., images of the slices, images of the residual slices, images of the lossy reconstructed slices, the 3D medical image, etc.).

According to a fourth aspect of the invention, there is provided a non-transitory computer-readable storage medium storing one or more programs configured to be executed by one or more processors. The one or more programs include instructions for performing or facilitating performing the method for compressing a 3D medical image or the method for decompressing compressed image data to obtain a 3D medical image, as mentioned above.

According to a fifth aspect of the invention, there is provided a method for processing medical image, which includes: (a) obtaining image data of a plurality of slices of a 3D medical image; (b) processing the image data of the plurality of slices, based on a relatively-lossy compression operation, to encode the image data of the plurality of slices to obtain a set of encoded slices data and decode the set of encoded slices data to obtain image data of a plurality of lossy reconstructed slices; (c) processing the image data of the plurality of slices and the image data of the plurality of lossy reconstructed slices to obtain residuals associated with differences between the image data of the plurality of slices and the image data of the plurality of lossy reconstructed slices; and (d) processing the residuals, based on a relatively-lossless compression operation, to encode the residuals to obtain a set of encoded residuals data. The set of encoded slices data and the set of encoded residuals data are operable for reconstruction of the plurality of slices.

The image data of the plurality of slices can be processed to form the plurality of slices, which can be displayed as images. The image data of the plurality of lossy reconstructed slices can be processed to form the plurality of lossy reconstructed slices, which can be displayed as images. The residuals can be processed to form a plurality of residual slices, which can be displayed as images. The number of the plurality of slices and the number of the plurality of lossy reconstructed slices may be the same. The number of the plurality of residual slices, the number of the plurality of slices, and the number of the plurality of lossy reconstructed slices may be the same.

For example, the set of encoded slices data may include encoded slices data bitstream, which is relatively-lossy. For example, the set of encoded residuals data may include encoded residuals data bitstream, which is relatively-lossless.

Optionally, the relatively-lossy compression operation and the relatively-lossless compression operation are arranged such that the set of encoded slices data and the set of encoded residuals data are operable for substantially visually lossless reconstruction of the plurality of slices (i.e., the reconstructed slices appear visually to be substantially lossless hence look substantially identical to the slices before the processing). Optionally, the relatively-lossy compression operation and the relatively-lossless compression operation are arranged such that the set of encoded slices data and the set of encoded residuals data are operable for substantially mathematically lossless reconstruction of the plurality of slices (i.e., the reconstructed slices are mathematically substantially lossless hence mathematically substantially identical to the slices before the processing). For example, the relatively-lossy compression operation and the relatively-lossless compression operation are arranged such that the set of encoded slices data and the set of encoded residuals data are operable for lossless reconstruction of the plurality of slices.

Optionally, step a) above includes processing the 3D medical image to convert the 3D medical image into the plurality of slices. For example, the processing of the 3D medical image may include partitioning the 3D medical image along an axis general perpendicular to a partition plane. Optionally, the partition plane is an axial/transverse plane. Optionally, the partition plane is a coronal plane. Optionally, the partition plane is a sagittal plane.

Optionally step a) above further includes receiving a user selection related to the axis and/or the partition plane, and the partitioning is based on the user selection. Optionally, the axial/transverse plane is the default partition plane.

In step b) above, the encoding may be performed using an encoder for the relatively-lossy compression and the decoding may be performed using a decoder for the relatively-lossy compression.

Optionally, the relatively-lossy compression operation is arranged to: reduce inter-slice redundancy for image data of at least some of the plurality of slices and/or reduce intra-slice redundancy for image data of at least some of the plurality of slices.

Optionally, the relatively-lossy compression operation is based on VVC.

Optionally, the relatively-lossy compression operation is based on HEVC.

Optionally, the relatively-lossy compression operation is based on H.264/MPEG-4 AVC.

Optionally, the relatively-lossy compression operation is based on AVS.

Optionally, the relatively-lossy compression operation includes: applying a hierarchical-B coding structure to image data of at least some of the plurality of slices to determine bi-directional (forward and backward) references for at least some of the plurality of slices, and performing bi-directional inter-prediction based on the bi-directional references. This may reduce inter-slice redundancy for image data of at least some of the plurality of slices.

Optionally, step c) above includes, for image data of each of the plurality of lossy reconstructed slices, respectively: determining a difference between image data of the lossy reconstructed slice and image data of a corresponding one of the slices to obtain a corresponding residual.

Optionally, the relatively-lossless compression operation is a substantially lossless compression operation. Optionally, the substantially lossless compression operation is a lossless compression operation.

Optionally, step d) above includes: sequentially encoding the residuals based on a hierarchical-B coding structure.

In step d), the encoding may be performed by an encoder for the relatively-lossless compression. Optionally, the encoder for the relatively-lossless compression utilizes an entropy model and an entropy encoder. Optionally, the entropy model contains a learning-based entropy model. Optionally, the entropy encoder contains an arithmetic encoder.

Optionally, the relatively-lossless compression operation includes: estimating probability distributions associated with the residuals using an entropy model and based on the image data of the plurality of lossy reconstructed slices and bi-directional (forward and backward) references, the bi-directional (forward and backward) references have been determined by applying a hierarchical-B coding structure to at least some of the plurality of slices; and compressing the residuals relatively-losslessly based on the estimated probability distributions. For example, the estimating of the probability distributions includes, for each of at least some of the residuals, respectively: estimating the probability distribution of a corresponding residual using the entropy model and based on bi-directional (forward and backward) references associated with the slice corresponding to the corresponding residual and a lossy reconstructed slice corresponding to the corresponding residual. For example, the compressing of the residuals includes, for each of at least some of the residuals, respectively: compressing the corresponding residual relatively-losslessly based on the corresponding estimated probability distribution. The compressing may be performed using an entropy encoder. Optionally, the entropy encoder includes an arithmetic encoder.

Optionally, the entropy model includes a learning-based entropy model.

Optionally, the estimating of the probability distributions associated with the residuals includes: generating context based on image data of the plurality of lossy reconstructed slices and the bi-directional (forward and backward) references, the context being operable as priors for the residuals; determining parameters for a parametrical probability model based on the generated context; and generating the probability distributions associated with the residuals using the parametrical probability model and based on the parameters. For example, the generating of the context includes, for each of at least some of the residuals, respectively: generating context based on image data of a corresponding lossy reconstructed slice and corresponding bi-directional (forward and backward) references, the context being operable as a prior for the corresponding residual. For example, the determining of the parameters includes, for each of at least some of the residuals, respectively: determining a corresponding parameter for a parametrical probability model based on the generated context. For example, the generating of the probability distributions includes, for each of at least some of the residuals, respectively: generating a corresponding probability distribution associated with the corresponding residual using the parametrical probability model and based on the corresponding parameter.

Optionally, the learning-based entropy model includes: an intra-slice and inter-slice context extraction module, a parameters estimation module, and the parametrical probability model.

Optionally, the generating of the context is performed using the intra-slice and inter-slice context extraction module.

Optionally, the determining of the parameters is performed using the parameters estimation module.

Optionally, the parameters estimation module includes stacked residual blocks.

Optionally, the parametrical probability model includes a discrete logistic mixture model.

Optionally, the intra-slice and inter-slice context extraction module includes: an intra-slice context extraction module, an inter-slice context extraction module, and a context fusion module.

Optionally, the generating of the context includes: (i) processing image data of the plurality of lossy reconstructed slices to generate lossy features; (ii) processing the bi-directional (forward and backward) references to generate bi-directional (forward and backward) features; (iii) processing the lossy features to generate intra-slice context; (iv) processing the bi-directional (forward and backward) features and the lossy features to generate inter-slice context; and (v) performing a context fusion operation to fuse the intra-slice context and the inter-slice context to generate the context. For example, the processing in (i) includes, for each of at least some of the residuals, respectively: processing image data of a corresponding lossy reconstructed slice to generate corresponding lossy feature. For example, the processing in (ii) includes, for each of at least some of the residuals, respectively: processing corresponding bi-directional (forward and backward) reference associated with image data of the slice corresponding to the corresponding lossy reconstructed slice to generate corresponding bi-directional (forward and backward) feature. For example, the processing in (iii) includes, for each of at least some of the residuals, respectively: processing the corresponding lossy feature to generate corresponding intra-slice context. For example, the processing in (iv) includes, for each of at least some of the residuals, respectively: processing the corresponding bi-directional (forward and backward) feature (and the corresponding lossy feature) to generate corresponding inter-slice context. For example, the processing in (v) includes, for each of at least some of the residuals, respectively: performing a context fusion operation to fuse the corresponding intra-slice context and the corresponding inter-slice context to generate a corresponding context for the corresponding lossy reconstructed slice.

Optionally, the processing in (i) is performed using stacked residual blocks.

Optionally, the processing in (ii) is performed using stacked residual blocks.

Optionally, the processing in (iii) is performed using the intra-slice context extraction module. Optionally, the intra-slice context extraction module includes a symmetry-based intra-slice context extraction module. Optionally, the symmetry-based intra-slice context extraction module includes stacked residual blocks and criss-cross self-attention module.

Optionally, the processing in (iv) is performed using the inter-slice context extraction module. Optionally, the inter-slice context extraction module includes a bi-directional inter-slice context extraction module. Optionally, the bi-directional inter-slice context extraction module includes: one or more linear layers, a bi-directional cross-attention model, and a feed-forward network.

Optionally, the context fusion operation includes channel-wise concatenation.

Optionally, the processing of the corresponding lossy feature to generate corresponding intra-slice context includes: performing a local correlation exploration operation based on the corresponding lossy feature and obtain corresponding local correspondence information; performing a global correlation exploration operation based on the corresponding local correspondence information to obtain corresponding global correspondence information; and generating corresponding intra-slice context based on the corresponding local correspondence information and the corresponding global correspondence information.

Optionally, the global correlation exploration operation includes: calculating similarity along directions generally perpendicular to two axes of symmetry, the two axes of symmetry being substantially perpendicular. For example, the calculating of the similarity may be based on a criss-cross query pattern.

Optionally, the local correlation exploration operation is performed using stacked residual blocks.

Optionally, the global correlation exploration operation is performed using a criss-cross self-attention module.

Optionally, the processing of the corresponding bi-directional (forward and backward) feature (and the corresponding lossy feature) to generate corresponding inter-slice context includes: processing corresponding forward reference feature to generate corresponding forward key feature and corresponding forward value feature; processing corresponding backward reference feature to generate corresponding backward key feature and corresponding backward value feature; processing corresponding lossy feature to generate corresponding query feature; processing the corresponding query feature, the corresponding forward key feature, the corresponding forward value feature, the corresponding backward key feature, and the corresponding backward value feature to generate corresponding inter-slice contextual feature; and processing the corresponding inter-slice contextual feature to generate corresponding inter-slice context.

Optionally, the processing of the corresponding forward reference feature is performed using a linear layer. Optionally, the processing of the corresponding backward reference feature is performed using a linear layer. Optionally, the processing of the corresponding forward reference feature and the processing of the corresponding backward reference feature is performed using the same linear layer. Optionally, the processing of the corresponding lossy feature is performed using a linear layer. Optionally, the processing of the corresponding query feature, the corresponding forward key feature, the corresponding forward value feature, the corresponding backward key feature, and the corresponding backward value feature is performed using a bi-directional cross-attention model. Optionally, the processing of the corresponding inter-slice contextual feature is performed using a feed-forward network.

Optionally, the processing the corresponding query feature, the corresponding forward key feature, the corresponding forward value feature, the corresponding backward key feature, and the corresponding backward value feature includes: multiplying the corresponding query feature and the corresponding forward key feature to generate a corresponding forward attention map; multiplying the corresponding forward value features and the corresponding forward attention map to generate corresponding forward contextual feature; multiplying the corresponding query feature and the corresponding backward key feature to generate corresponding backward attention map; multiplying the corresponding backward value features and the corresponding backward attention map to generate corresponding backward contextual feature; and using the corresponding forward contextual feature and the corresponding backward contextual feature to generate corresponding inter-slice contextual feature.

Optionally, the fusing includes channel-wisely concatenating the corresponding forward contextual feature and the corresponding backward contextual feature to generate corresponding inter-slice contextual feature.

Optionally, the method further includes: storing the set of encoded slices data and the set of encoded residuals data as one or more data files.

Optionally, the 3D medical image is a CT image. Optionally, the 3D medical image is a MRI image. The 3D medical image may be 3D medical image of other imaging modality (other than CT and MRI).

According to a sixth aspect of the invention, there is provided a method for processing medical image, including: (i) processing a set of encoded slices data, based on a relatively-lossy decompression operation, to obtain image data of a plurality of lossy reconstructed slices; (ii) processing a set of encoded residuals data, based on a relatively-lossless decompression operation, to obtain reconstructed residuals; and (iii) processing the image data of the plurality of lossy reconstructed slices and the reconstructed residuals to obtain image data of a plurality of slices that generally correspond to a combination (e.g., by addition) of the image data of the plurality of lossy reconstructed slices and the image data of the reconstructed residuals. The image data of the plurality of slices are operable for reconstruction of a 3D medical image.

The image data of the plurality of slices can be processed to form the plurality of slices, which can be displayed as images. The image data of the plurality of lossy reconstructed slices can be processed to form the plurality of lossy reconstructed slices, which can be displayed as images. The reconstructed residuals can be processed to form a plurality of reconstructed residual slices, which can be displayed as images. For example, the number of the plurality of slices and the number of the plurality of lossy reconstructed slices may be the same. For example, the number of the plurality of residual slices, which can be displayed as images, the number of the plurality of slices, and the number of the plurality of lossy reconstructed slices may be the same.

For example, the set of encoded slices data may include encoded slices data bitstream, which is relatively-lossy. For example, the set of encoded residuals data may include encoded residuals data bitstream, which is relatively-lossless.

Optionally, the relatively-lossless decompression operation is a substantially lossless decompression operation. Optionally, the substantially lossless decompression operation is a lossless decompression operation.

Optionally, the set of encoded slices data is obtained using the method of the fifth aspect.

Optionally, the set of encoded residuals data is obtained using the method of the fifth aspect.

Optionally, step (i) above is performed using a decoder for the relatively-lossy decompression which: has the substantially same architecture as the decoder for the relatively-lossy compression or is the decoder for the relatively-lossy compression.

Optionally, step (ii) above is performed using a decoder for the relatively-lossless decompression which: has the substantially same architecture as the encoder for the relatively-lossless compression or is the encoder for the relatively-lossless compression.

Optionally, the method further includes: processing the image data of the plurality of slices to convert the image data of the plurality of slices into the 3D medical image. For example, the processing may include stacking or combining the image data of the plurality of slices to form the 3D medical image.

In a seventh aspect, there is provided a method for processing medical image, containing: performing the method of the fifth aspect, and performing the method of the sixth aspect.

Other features and aspects will become apparent by consideration of the detailed description and accompanying drawings. Any feature(s) described herein in relation to one aspect or embodiment may be combined with any other feature(s) described herein in relation to any other aspect or embodiment as appropriate and applicable.

Terms of degree such that "generally", "about", "substantially", or the like, are used, depending on context, to account for manufacture tolerance, degradation, trend, tendency, imperfect practical condition(s), etc. For example, when a value is modified by terms of degree, such as "about", such expression may include the stated value $\pm 20\%$, $\pm 15\%$, $\pm 10\%$, $\pm 5\%$, $\pm 2\%$, or $\pm 1\%$.

One can see that embodiments of the invention therefore provide effective compression/decompression schemes for 3D medical images that utilize both lossy and lossless compressions to different components of the medical image. With the lossy-then-lossless compression pipeline, the smooth contents of 3D medical images are effectively encoded by the lossy compression, and the residues containing intricate details are further handled by the lossless compression. Experimental results on prevailing 3D medical image datasets demonstrate that the method according an exemplary embodiment of the invention achieve promising compression performance and outperforms state-of-the-art methods.

The foregoing summary is neither intended to define the invention of the application, which is measured by the claims, nor is it intended to be limiting as to the scope of the invention in any way.

BRIEF DESCRIPTION OF FIGURES

The foregoing and further features of the present invention will be apparent from the following description of embodiments which are provided by way of example only in connection with the accompanying figures, of which:

FIG. 11 is a table showing performance comparisons between the proposed method and some prior art methods on the MRNet dataset.

In the drawings, like numerals indicate like parts throughout the several embodiments described herein.

DETAILED DESCRIPTION

Figure 1A:
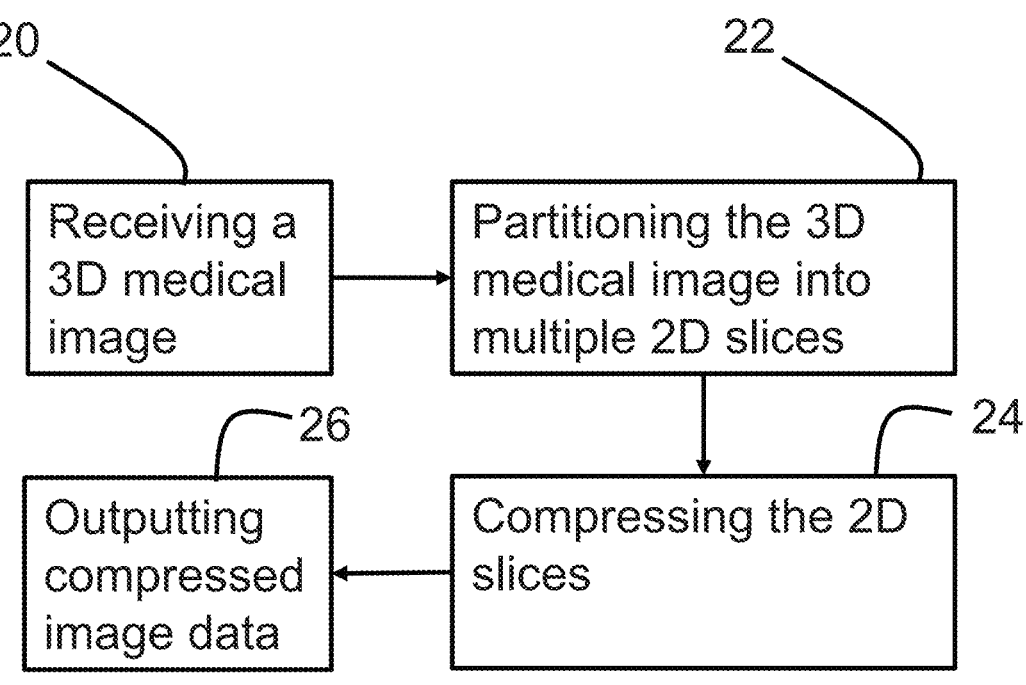
FIG. 1*a* shows a schematic diagram of a system/method for compressing a 3D medical image according to a first embodiment of the invention.

Referring now to FIG. 1a, which shows a high-level schematic diagram for a system/method of compressing a 3D medical image according to a first embodiment of the invention. Examples of the 3D medical image include CT medical images and MRI medical images of human body (e.g., knee, lung, brain) or animal body. The blocks in FIG. 1a can be considered either as method steps, or function modules of the system that carry out the illustrated functions. The system and its function modules can be implemented using hardware and/or software. Using the method steps as a basis of description, the method in FIG. 1a starts with Step 20 in which a 3D medical image is received by the system as input data, and the goal of the method is to efficiently compress the 3D medical image for file storage or for transmission (e.g. as streamed data over a communication network). In Step 22, the 3D medical image is portioned into a plurality of 2D slices, which facilitate the compression process. Next, in Step 24 the 2D slices are processed to provide encoded or compressed image data, and finally in Step 26 the compressed image data is outputted for storage or transmission. Details of these method steps according to exemplary embodiments of the invention will be described later.

Figure 1B:
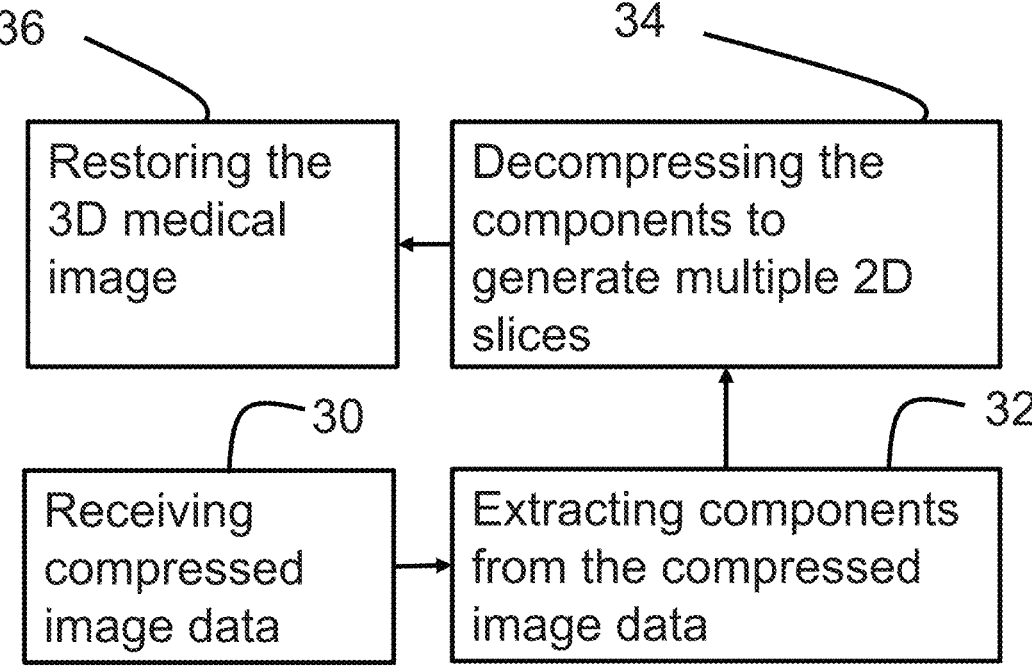
FIG. 1*b* shows a schematic diagram of a system/method for decoding compressed image data to restore a 3D medical image according to a second embodiment of the invention.

FIG. 1b shows a reversed process of that in FIG. 1a, and in FIG. 1b compressed image data (for example the output of the system in FIG. 1a) is decompressed/decoded in order to restore a 3D medical image. The method in FIG. 1b starts with Step 30, in which a compressed image data is received by the system (e.g., from a digital file, or from a data stream transmitted over a network. Next, in Step 32 different components (e.g., layers) of the compressed image data are extracted, and in Step 34 the components are decompressed in order to generate a plurality of 2D slices. Finally the plurality of 2D slices are combined to obtain the restored 3D medical image. Again, details of these method steps according to exemplary embodiments of the invention will be described later.

Figures 2A, 2B:
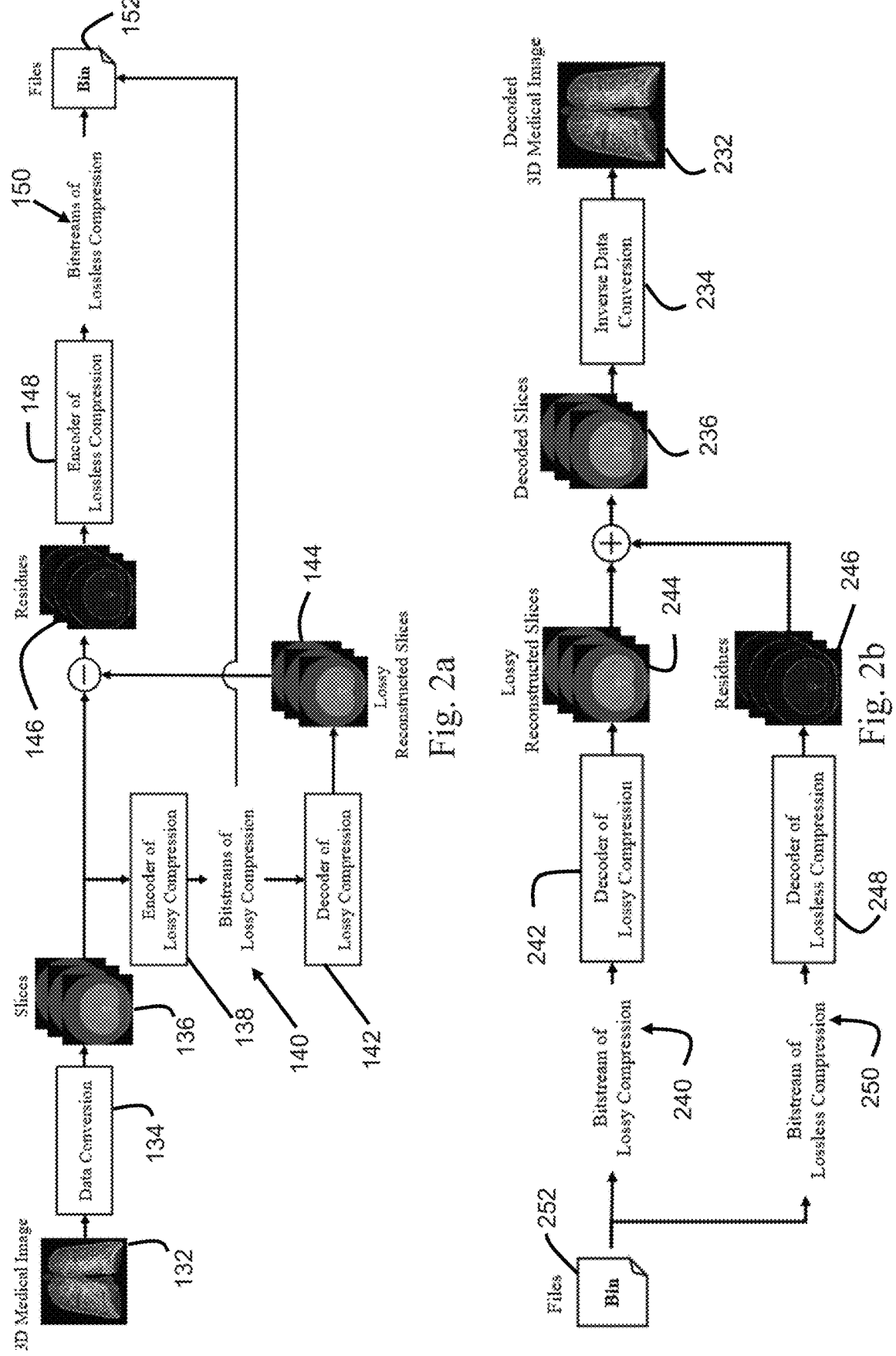
FIG. 2a shows a framework of a system/method for compressing a 3D medical image according to a further embodiment of the invention.
FIG. 2b shows a framework of a system/method for decoding compressed image data to restore a 3D medical image according to a further embodiment of the invention.

Turning to FIG. 2a, which shows another embodiment of the invention that generally follows the structure of the method/system in FIG. 1a, but with particulars of compressing methods used for a 3D medical image. As shown in FIG. 2a, in this embodiment, an input 3D medical image 132 is first partitioned into a plurality of first slices 136 (which are 2D slices) by a data conversion module 134. Then, the first slices 136 are compressed in a lossy-to-lossless paradigm (lossy phase+lossless phase. In the lossy compression phase, an encoder of lossy compression 138 is applied to the first slices 136 to encode the same with a lossy codec to yield compact bitstreams (which are the bitstreams of lossy compression 140 as shown in FIG. 2a), in which bi-directional references (not shown) are used to reduce inter-slice redundancy. Afterwards, a decoder of lossy compression 142 is applied to the bitstreams of lossy compression 140 to obtain lossy reconstructed slices 144, which are a second set of 2D slices originated but different from the first slices 136. Each of the lossy reconstructed slices 144 corresponds to a respective one of the first slices 136. The lossy reconstructed slices 144 are then each compared with the first slices 136 to determine residuals (differences) 146 between the lossy reconstructed slices 144 and the first slices 136. Again, there is a plurality of residuals 146, each of which corresponds to one of the first slices 136 and a corresponding one of the lossy reconstructed slices 144. In the lossless phase, an encoder of lossless compression 148 is used to compress the residuals 146 to bitstreams of lossless compression 150 using a lossless codec, which utilizes the bi-directional references. Finally, the bitstreams of lossless compression 150 and the bitstreams of lossy compression 140 are merged and written into files 152 for storage. Similar to what is mentioned above, each of the data conversion module 134, the encoder of lossy compression 138, the decoder of lossy compression 142, and the encoder of lossless compression 148 may be implemented by hardware modules, software modules, or they may even be implemented by the same hardware/software (e.g., different sub-routines of software). In addition, although in FIG. 2a the encoder of lossy compression 138, the decoder of lossy compression 142, and the encoder of lossless compression 148 are shown as different components, they could be in fact a same encoder/decoder module which processes the different tasks at different stages of the method.

FIG. 2b shows a reversed process of that in FIG. 2a, and in FIG. 2b compressed image data (for example the output of the system in FIG. 2a) stored in files 252 is decompressed in order to restore a 3D medical image 232. In particular, the received compressed image data is first processed to extract a bitstream of lossy compression 240, and a bitstream of lossless compression 250. The bitstream of lossy compression 240 is then decoded by a decoder of lossy compression 242 using a lossy codec to obtain lossy reconstructed slices 244. In parallel, the bitstream of lossless compression 250 is decoded by a decoder of lossless compression 248 to obtain a plurality of residues 246. Each of the plurality of residuals 246 corresponds to one of the lossy reconstructed slices 244. Then, each residual 246 is added to or combined with a corresponding one of the lossy reconstructed slices 244, in this way a plurality of decoded slices 236 is obtained, which are generally identical (at least substantially visually lossless, or even substantially mathematically lossless) to original slices that were used to generate the compressed image data. Then, the plurality of decoded slices 236 is processed by an inverse data conversion module 234 to assemble the decoded slices 236 to form a reconstructed 3D medical image 232.

Similar to the what is mentioned above, each of the inverse data conversion module 234, the decoder of lossy compression 242, and the decoder of lossless compression 248 may be implemented by hardware modules, software modules, or they may be implemented even by the same hardware/software (e.g., different sub-routines of software). In addition, although in FIG. 2b the decoder of lossy compression 242 and the decoder of lossless compression 248 are shown as different components, they could be in fact a same encoder/decoder module that processes the different tasks at different stages of the method. What is more, the systems respectively shown in FIGS. 2a-2b may be physically separated systems for example those located remotely from each other over a communication network. Or, the systems may be actually a single system that is configured to conduct both compression and depression works. On this basis, an encoder in FIG. 2a may actually also be the corresponding decoder in FIG. 2b which utilizes a corresponding codec (e.g., for lossy or lossless compression/decompression). In some of these embodiments, the 3D medical image compression and decompression frameworks in FIGS. 2a and 2b may be based at least in part on deep learning.

In one embodiment, the data conversion module 134 in FIG. 2a is designed to convert a 3D medical image $X \in R^{H \times W \times D}$ into a set of 2D slices $Y=\{y_1, y_2, \ldots, y_N\}$. Specifically, the partition plane may be selected among the axial plane $R^{H \times W}$, the coronal plane $R^{W \times D}$ and the sagittal plane $R^{H \times D}$, then, $X \in R^{H \times W \times D}$ is partitioned to 2D slices along the axis perpendicular to the selected partition plane. In one embodiment, the inverse data conversion module 234 in FIG. 2b is used to provide 3D medical image by stacking the decoded 2D slices along the axis perpendicular to selected partition plane.

Figure 3:
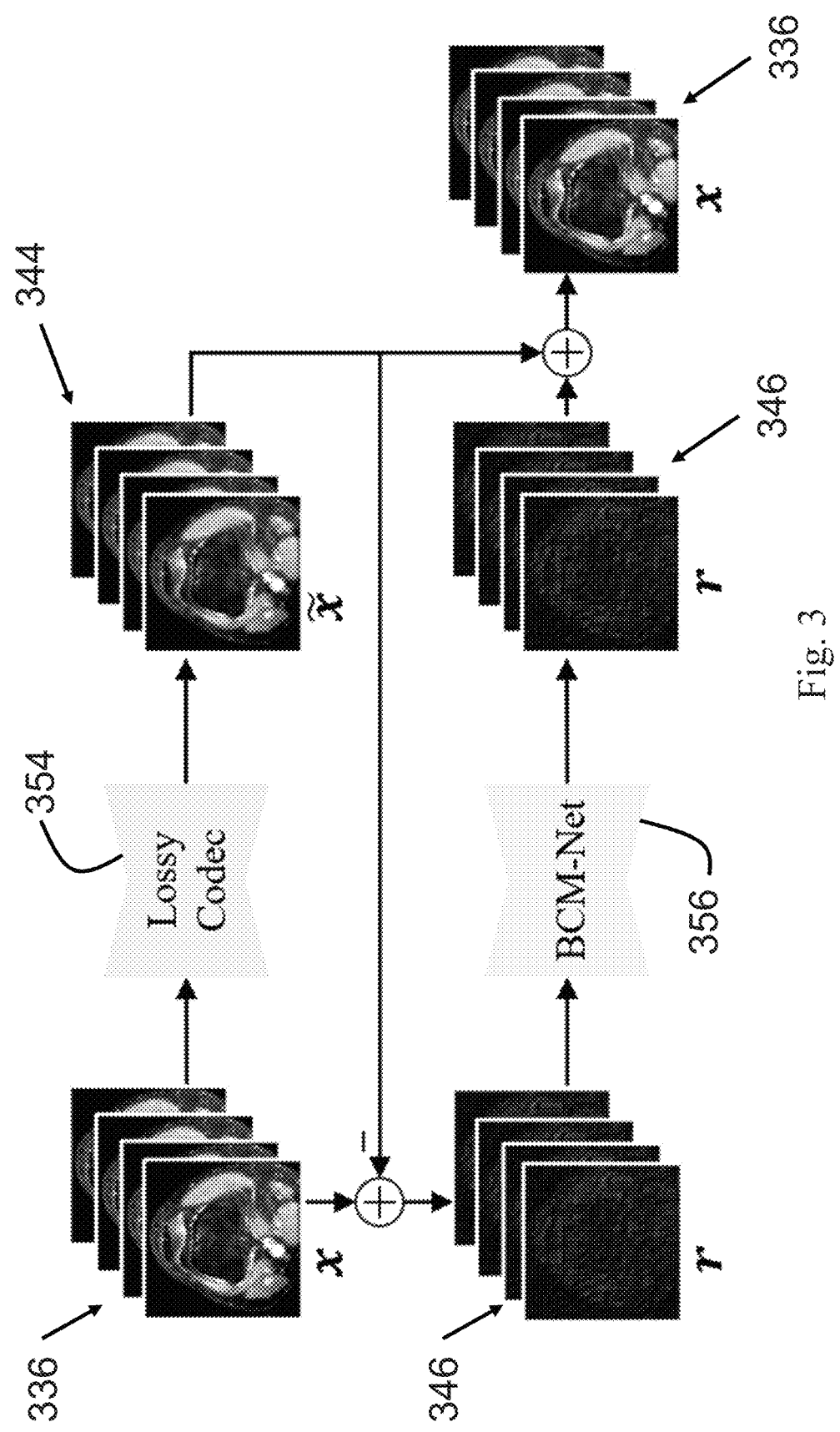
FIG. 3 is an overview of a 3D medical image lossless compression/decompression framework according to a further embodiment of the invention.

FIG. 3 shows a lossless and lossy compression/decompression framework according to another embodiment of the invention, which may be used in the systems of FIGS. 1a-2b. When used in the system of FIG. 2a, the framework in FIG. 3 may perform the part of the compression process that starts with the first slices 136, until the generation of the bitstreams of lossless compression 150 and the bitstreams of lossy compression 140. When used in the system of FIG. 2b the framework in FIG. 3 may perform the part of the decompression process that starts with extracted bitstreams of lossless compression 250 and the bitstreams of lossy compression 240, until the generation of the decoded slices 236.

In summary, the framework in FIG. 3 makes use of residual coding that has a considerable impact on coding performance, in which a lossy layer is initially employed and the reconstruction errors (i.e., the residues) are then losslessly compressed. The underlying principle of the residual coding revolves around the exploration of priors based on context modeling. For residual coding, the prevalent bilateral correlations in 3D medical images are exploited from the perspective of the inherent anatomical symmetry within each slice and the bi-directional reference relationship between slices. Owing to the effective prior information provided by the bilateral context modeling mechanism, the lossless compression network can accurately estimate the distributions of residuals, thereby achieving efficient compression.

In one implementation, the residual coding framework in FIG. 3 involving the lossy codec 354 based on an off-the-shelf video codec (such as VVC, HEVC, H.264/MPEG-4 AVC, or AVS) as the lossy layer, and a Bilateral Context Modeling based Network (BCM-Net) 356 as the residual layer. The BCM-Net 356 is developed by incorporating the specific bilateral priors in 3D medical images, showing superior performance in reducing redundancies. Therefore, the BCM-Net 356 is adapted to achieve efficient lossless compression of residues through exploring intra-slice and inter-slice bilateral contexts. In particular, in one implementation a SICE module (not shown in FIG. 3) is configured to mine bilateral intra-slice correlations rooted in the inherent anatomical symmetry of 3D medical images, and a bi-directional inter-slice context extraction (BICE) module (not shown in FIG. 3) is configured to explore bilateral inter-slice correlations from bi-directional references, thereby yielding representative inter-slice context. Thus, the framework in FIG. 3 involves a comprehensive exploration of inter-slice priors within 3D medical images, leveraging bi-directional referencing and dedicated network design to improve coding efficiency. Experiments on popular 3D medical image datasets demonstrate that such a framework can outperform existing state-of-the-art methods owing to efficient redundancy reduction.

Details of the BCM-Net, the SICE module, the BICE module, and the experiment results will be discussed in greater details later. However, firstly some traditional medical image compression techniques will now be described. Traditional lossless 3D image compression methods can be classified into 3D transform-based methods and sequence-based methods. Despite the notable compression efficiency achieved by traditional lossless 3D medical image compression methods, they are limited by the hand-crafted design, which cannot be optimized in a data-driven fashion to accommodate 3D medical images. On the other hand, learned lossless 3D image compression methods can be broadly classified into two categories: 3D transform-based methods and sequence-based methods. In comparison to traditional methods, learned lossless 3D medical image compression methods enable adaptive modeling of characteristics of 3D medical images, resulting in superior performance. Nevertheless, the inherent bilateral correlations of 3D medical images have not been effectively exploited yet, leaving considerable potential for performance improvement through efficient utilization of such characteristics. Moreover, neural video coding methods can be divided into deep coding tools that are incorporated into traditional coding schemes, and deep coding frameworks that can be optimized in an end-to-end manner. Notably, deep video coding frameworks have attained competitive performance as compared to traditional video coding methods and demonstrated huge potential.

In the prevalent residual coding paradigm depicted in FIG. 3, to effectively encode original slices 336 of a 3D medical images, these original slices 336 are first encoded by the lossy codec 354, and residues 346 between original slices 336 and lossy reconstructions 344 are then compressed by the dedicated BCM-Net 356 to obtain a plurality of encoded residues (not shown in FIG. 3). Specifically, for the original slice 336 set x={x1, . . . , $x_t$, . . . $x_T$} of length T, the video codec of VVC as the lossy codec 354 is first employed to encode x into bitstreams and generate lossy reconstructions $\tilde{x}=\{\tilde{x}_1, \ldots, \tilde{x}_t, \ldots, \tilde{x}_T\}$. Subsequently, the BCM-Net 356 is employed to losslessly compress residues r={$r_1$, . . . , $r_t$, . . . , $r_T$} where $r_t=x_t-\tilde{x}_t$. In the lossless compression, residues r are partitioned into several group of pictures (GOP), and residual signals within each GOP are sequentially encoded based on the hierarchical B-frames coding structure [60] depicted in FIG. 4. In the BCM-Net 356, bilateral correlations are explored from lossy reconstructions 344 and bi-directional references (not shown in FIG. 3), where the bi-directional references are also provided by previously decoded slices (i.e., the lossy reconstructions 344), yielding representative intra-slice and inter-slice contexts. Then, entropy coding is performed to encode residues 346 to bitstreams based on contexts, where the bitstreams represent the plurality of encoded residues. Bitstreams yielded respectively by the lossy and residual layers are merged and transmitted to the decoder side.

At the decoder side, the received bitstreams are first spliced, in which bitstreams corresponding to lossy layer is used as the input to the decoder that is also based on the video codec of VVC as the lossy codec 354 to generate x̃, and remaining bitstreams is fed to BCM-Net 356 to generate decoded residues r that are shown by part number 346 in FIG. 3. Regarding the decoding with the BCM-Net 356, encoded residues are sequentially decoded following the same order as encoding, which enables bi-directional references for the residues. In specific, bi-directional references and lossy reconstructions are jointly used to generate intra-slice and inter-slice contexts, followed by the entropy decoding based on contexts to generate the decoded residues r. Then, r and x̃ are added to generate reconstructed slices 9 that are shown by part number 336 in FIG. 3, which are identical to the original version x̂. Finally, the decoded slices 336 are merged to generate the reconstructed 3D medical image.

Figure 5:
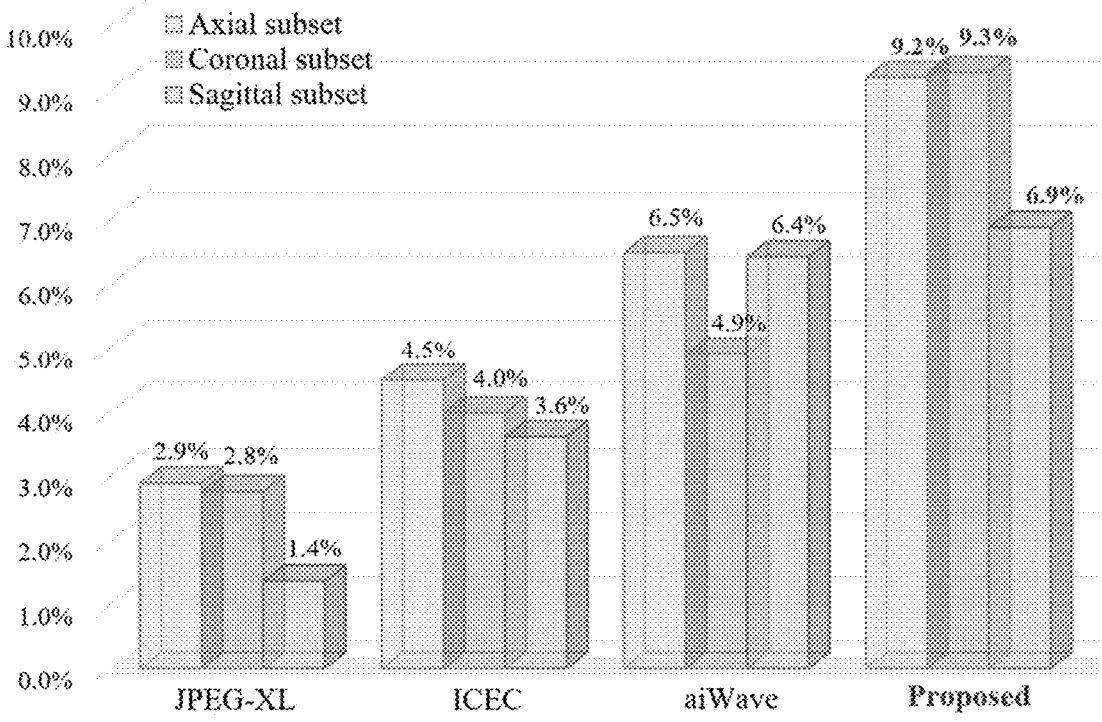
FIG. 5 shows the performance comparisons of the compression framework in FIG. 3 and some prior art methods.
Figure 6:
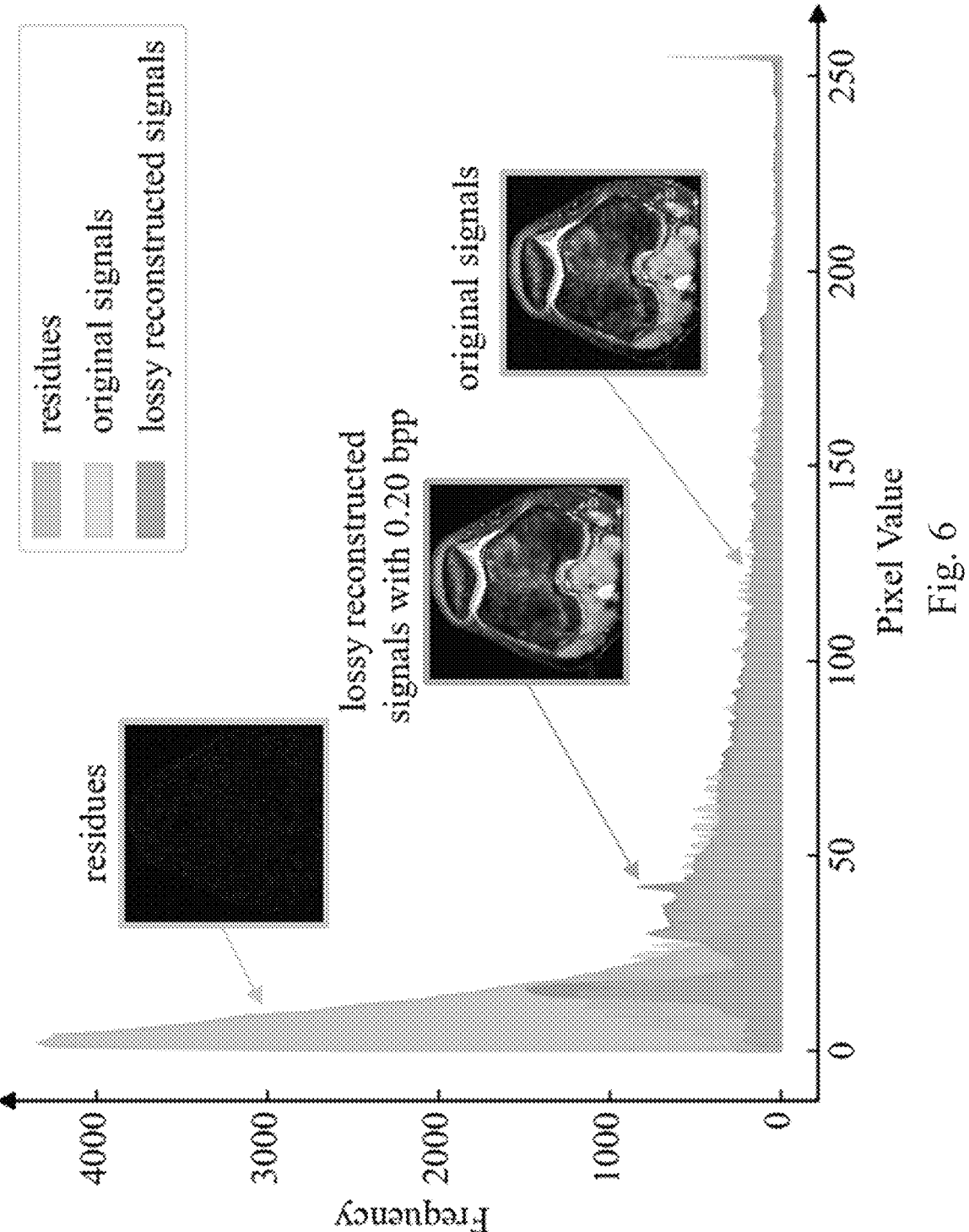
FIG. 6 illustrates visualizations and histograms of original signals, lossy reconstructed signals and residues, in which the lossy reconstructed signals can provide effective prediction with marginal bit consumption (4% of total bit consumption).
Figure 7:
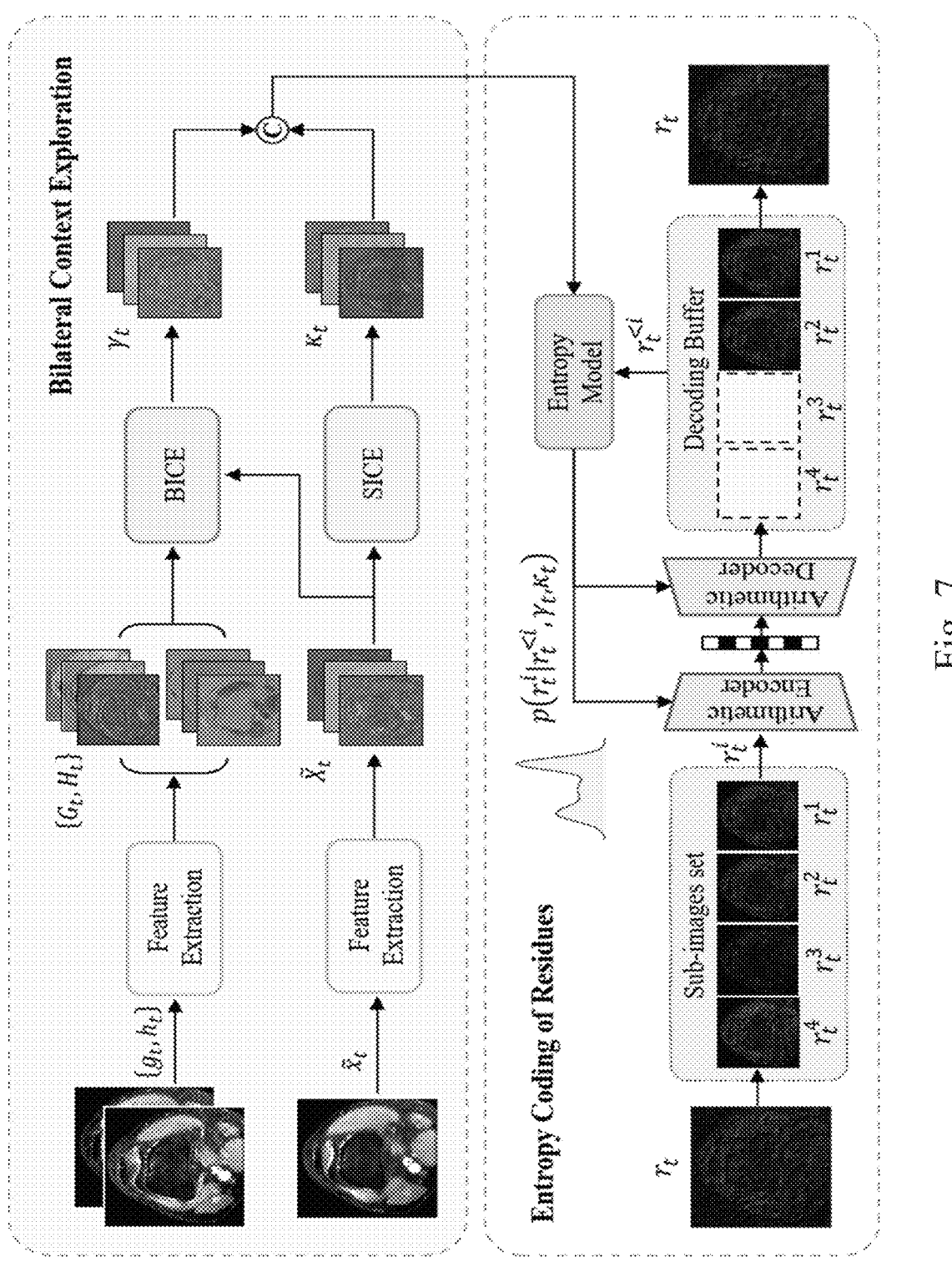
FIG. 7 is an illustration of an architecture of the deep residual coding network with bilateral context modeling, according to an embodiment of the invention.
Figure 9:
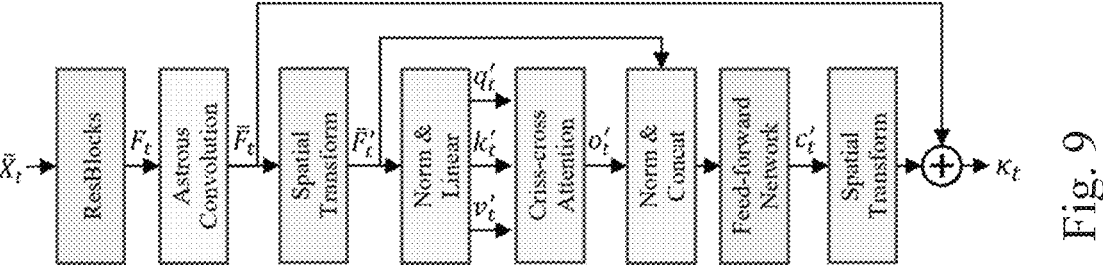
FIG. 9 shows the architecture of the SICE module according to one embodiment of the invention.
Figure 10:
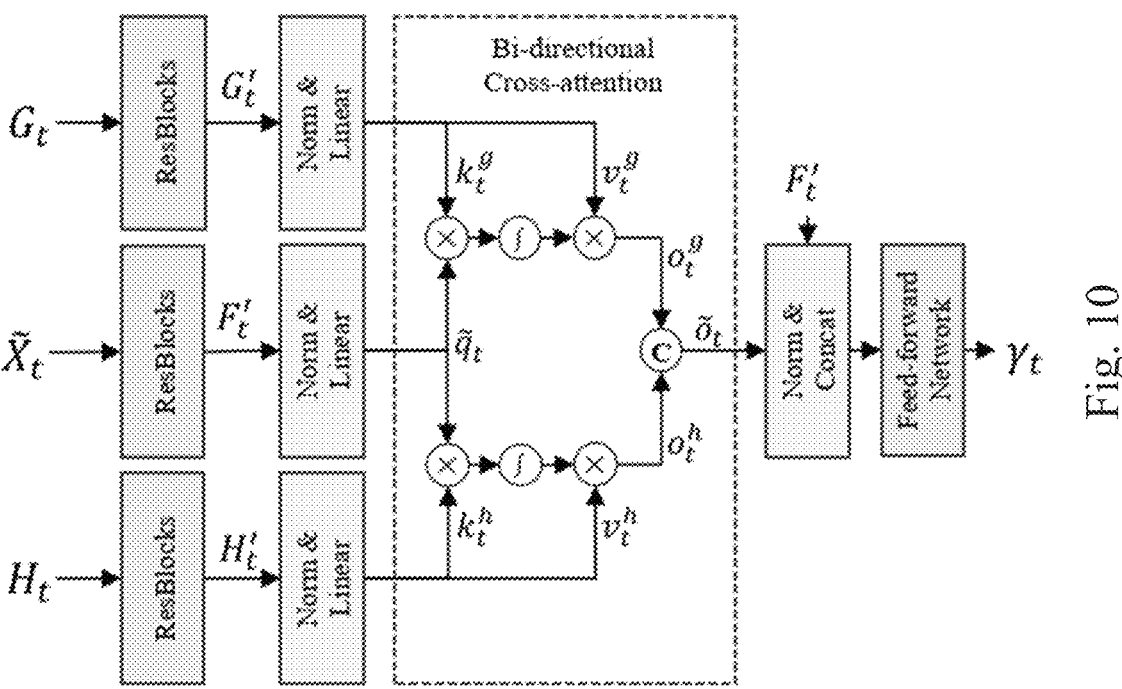
FIG. 10 shows the architecture of the BICE module according to one embodiment of the invention.

There are several advantages of the dedicated 3D medical image lossless compression framework in FIG. 3. First, this framework exhibits extensive adaptability with existing 3D medical image processing pipelines since the existing standard-compatible (e.g., VVC) codecs can be directly employed for the lossy layer without necessitating modifications. Second, the framework can provide not only lossless reconstructions to support a meticulous diagnosis but also lossy reconstructions to enable skimming by physicians. Third, as shown in FIG. 6, the lossy layer can provide accurate prediction with marginal bit consumption. As such, the coding of residues which cannot be represented in the base layer becomes prominent. In addition, FIG. 5 illustrates performance comparison between the framework shown in FIG. 3 (indicated as "proposed" or "proposed method" in FIG. 3 and in the following part of the description) that incorporates various modules as shown in FIGS. 7, 9-10, and some prior art methods, on the three subsets of MRNet dataset [32], where FLIF [33] is used as the anchor to calculate bitrate saving ratio. Among comparison methods, JPEG-XL [19] is the most advanced traditional lossless image compression method, while ICEC [30] and aiWave [31] are the state-of-the-art learned lossless compression methods for 3D medical image.

Next, the principles of the BCM-Net based residual coding and algorithms involved will be described in details. Overall speaking, the efficiency of residual coding overwhelmingly depends on the efficacy of prior information provided by contexts. To facilitate residual coding, the BCM-Net is devised, exploring bilateral correlations from lossy reconstructions and bi-directional references to generate representative contextual priors. Specifically, as illustrated in FIG. 7, intra-slice features $\tilde{X}_t$ are first extracted from lossy reconstructions $\tilde{x}_t$, and inter-slice features {$G_t$, $H_t$} are extracted from bi-directional reference slices {$g_t$, $h_t$}, which are collected from previously decoded slices based on the hierarchical B-frames coding structure shown in FIG. 4. Then, the SICE module is devised to effectively mine intra-slice prior information from $\tilde{X}_t$ based on the characteristic of anatomical symmetry, yielding intra-slice context $\kappa_t$. Meanwhile, sufficient inter-slice prior information is explored from {$G_t$, $H_t$} by the BICE module, yielding inter-slice context $\gamma_t$. The contexts {$\kappa_t$, $\gamma_t$} are jointly employed as effective priors for the compression of residues $r_t$.

In the entropy coding of $r_t$, an auto-regressive dependency is established among pixels of $r_t$, enabling exploration of spatial correlations based on previously decoded pixels of $r_t$. More specifically, pixels in $r_t$ are grouped into four sub-images $$\{r_t^1, r_t^2, r_t^3, r_t^4\}$$

by the polyphase decomposition [62], followed by the sequential compression of sub-images. Correspondingly, estimated distributions of residues $p(r_t|\kappa_t, \gamma_t)$ can be factorized as $$p(r_t|\kappa_t, \gamma_t) = p(r_t^1|\kappa_t, \gamma_t) \cdot \prod_{i=2}^{4} p(r_t^i|r_t^{<i}, \kappa_t, \gamma_t), \tag{1}$$

in which $$r_t^{<i}$$

denotes previous decoded sub-images. Then, with the aim of feasible estimation of the probability in Eqn. (1), the entropy model is devised to parametrically model probability distributions of each sub-image $$r_t^i \in \{r_t^1, r_t^2, r_t^3, r_t^4\},$$

in which parameters are estimated based on priors $$r_t^{<i},$$

$\kappa_t$ and $\gamma_t$. This process can be formulated as $$p\left(r_t^i \big| r_t^{<i}, \kappa_t, \gamma_t\right) = \mathcal{P}\left(\mu_t^i, \sigma_t^i, \pi_t^i\right), \tag{2}$$

$$\text{with } \mu_t^i, \sigma_t^i, \pi_t^i = \mathcal{E}\left(r_t^{<i}, \kappa_t, \gamma_t\right),$$

in which $p\left(\cdot\right)$ denotes the discrete logistic mixture probability model [22], $$\left\{\mu_t^i, \sigma_t^i, \pi_t^i\right\}$$

denote the parameters of $p\left(\cdot\right)$ and $\varepsilon(\cdot)$ denotes the parameter estimation network. The arithmetic coding algorithm [63] is then employed to encode sub-image based on the estimated probability distributions. In the decompression of residues, sub-images are sequentially decoded by the arithmetic decoder and assembled to decoded residues.

Figure 8:
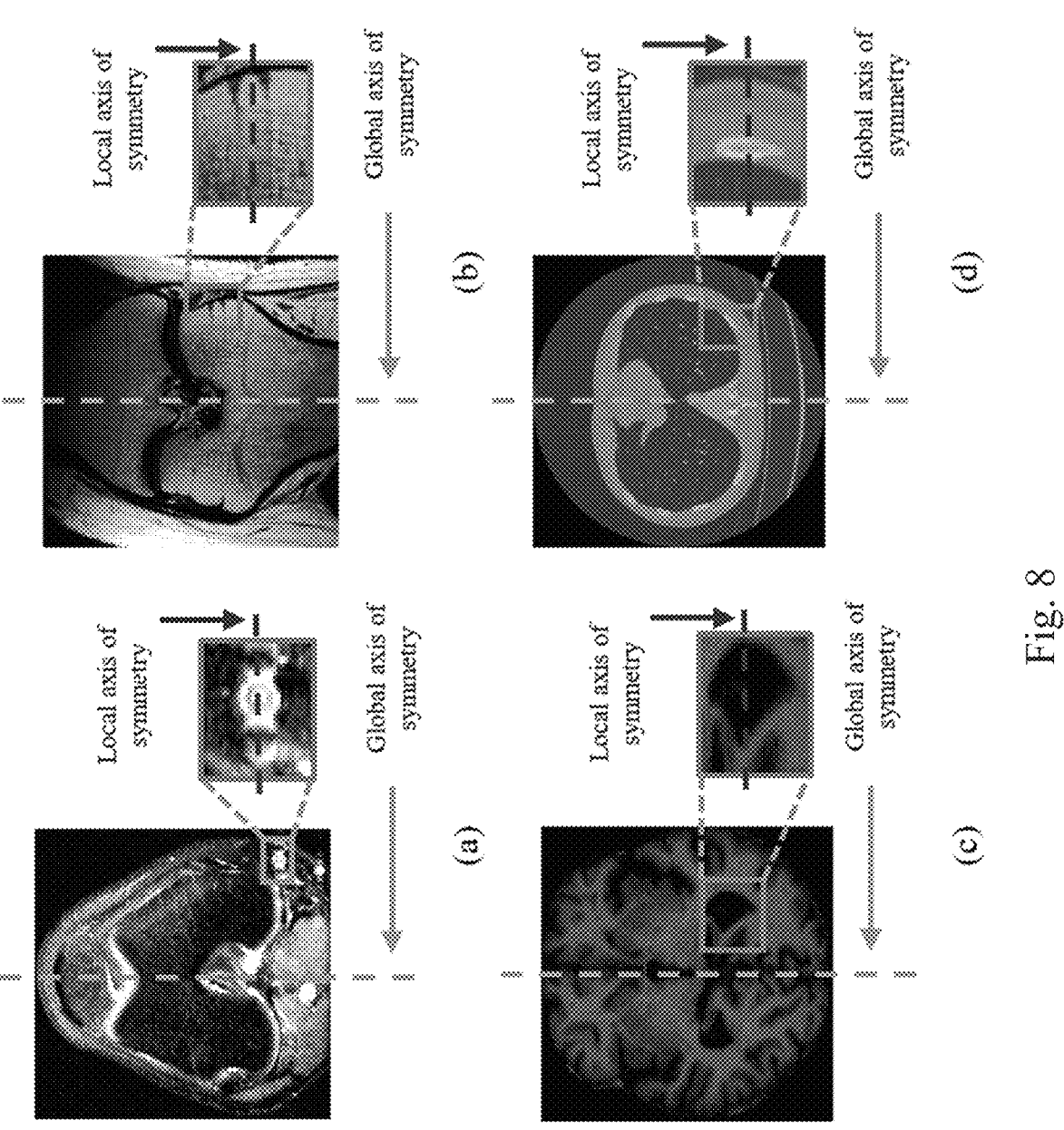
FIG. 8 is an illustration of global and local symmetry in slices from several datasets of medical images.

The symmetry-based intra-slice context extraction will now be described. Symmetric structures and textures are prominent in 3D medical images due to the inherent anatomical symmetry of the human body. In particular, as illustrated in FIG. 8, slices of medical images exhibit significant local and global symmetries, wherein the former arises from the local-symmetric properties of tissues and the latter originates from the bilateral symmetry of the human body. Additionally, owning to the registration preprocessing [64] in 3D medical image acquisition, the global symmetry is typically represented as being symmetric about principal axes, i.e., the vertical axis and horizontal axis. Owing to such bilateral symmetries in 3D medical images, notable intra-slice structural and textural similarities are exhibited in the lossy reconstructions, which can be leveraged as effective prior knowledge to facilitate residual coding. Therefore, the SICE module is proposed to capture bilateral intra-slice correlations based on anatomical symmetry and generate representative intra-slice context.

As shown in FIG. 9, the SICE module according to one embodiment of the invention accepts features of lossy reconstruction $\tilde{X}_t$ as inputs and outputs intra-slice context $\kappa_t$. The SICE module begins with the extraction of initial features $F_t$ from $\tilde{X}_t$ via residual blocks, followed by the exploration of local and global symmetrical correlations. Specifically, due to the fact that local symmetry of tissues typically exists in separate local regions and directions of the local axes of symmetry vary among these regions, implicitly mining local symmetries is considered by aggregating neighborhood information in features Ft. Particularly, the atrous convolution [22] with a multi-scale receptive field is leveraged to aggregate localized information from multi-scale neighbor regions of $F_t$, generating a feature $\overline{F}_t$ that contains local contextual information. Additionally, to generate representative intra-slice context, long-range correlations stemming from global anatomical symmetry are further explored. Specifically, the spatial transform network [67] is first used to enhance $\overline{F}_t$ by transforming $\overline{F}_t$ based on a learnable affine matrix. Then, layer normalization [68] and linear projection are employed to the enhanced features $$\overline{F}_t'$$

to derive the feature triplet $$\left\{q_t', k_t', v_t'\right\},$$

i.e.

$$q_t', k_t', v_t' = \mathcal{W}\left(\mathcal{N}\left(\overline{F}_t'\right)\right), \tag{3}$$

in which $\mathcal{N}\left(\cdot\right)$ denotes the layer normalization and $w\left(\cdot\right)$ denotes the linear projection. Subsequently, since the global correlations of slices exhibit as being symmetric about the principal axes, the criss-cross attention [69] is performed to capture axial-symmetric correlations based on $$\left\{q_t', k_t', v_t'\right\}.$$

Based on the criss-cross pattern in the attention module, for each query token in $$q_t',$$

axial-symmetric reference tokens are collected from $$k_t'$$

along directions orthogonal to the principal axes as candidates for the symmetry point of the query token. Then, the similarities between the query token and its reference tokens are calculated and further leveraged to aggregate contextual information from $$v_t',$$

producing output features $$o_t'$$

with axial-symmetric correlations. The output features $$o_t'$$

are then normalized, concatenated with $$\overline{F}_t',$$

and fed into the feed-forward network [68] to generate context features $$c_t'.$$

This process can be formulated as $$o'_t = C(q'_t, k'_t, v'_t),$$ (4)

$$c'_t = \mathcal{F}(\overline{F}'_t \oplus \mathcal{N}(o'_t)),$$

in which C(·) denotes the criss-cross attention, ⊕ denotes the channel-wise concatenation and F(·) denotes the feed-forward network. Then, the spatial transform network is used to enhance $c'_t$, and the enhanced features are further added with $\overline{F}_t$ to generate intra-slice context $\kappa_t$.

The SICE module can efficiently capture bilateral intra-slice correlations in $\tilde{X}_t$ based on the prevalent anatomical symmetry. In particular, the local correlations are first explored by aggregating neighbor information in $\tilde{X}_t$. Then, the global correlations are mined by the long-range dependency exploration along the symmetric axis. Moreover, both the local and the global anatomical symmetries are involved to facilitate the exploration of intra-slice correlations, resulting in the effective intra-slice context $\kappa_t$ for the compression of residues $r_t$.

Next, the bi-directional inter-slice context extraction will be discussed. Due to the continuous scanning in 3D medical image acquisition, there exist significant bilateral correlations between neighbor slices. To this end, the BICE module is designed to explore inter-slice correlations from bi-directional references to generate an effective context for residual coding.

As illustrated in FIG. 10, the proposed BICE module takes features $\tilde{X}_t$ of lossy reconstruction and features {$G_t$, $H_t$} of bi-directional references as inputs, and generates inter-slice context $\gamma_t$ for the lossless compression of $r_t$. Specifically, residual blocks are first applied to {$G_t$, $H_t$} and $\tilde{X}_t$ to extract features, i.e., $$F'_t = \mathcal{R}(\tilde{X}_t),$$ (5)

$$G'_t = \mathcal{R}(G_t),$$

$$H'_t = \mathcal{R}(H_t),$$

in which R(·) denotes the residual blocks. Query, key and value features are then generated from the extracted features by layer normalization and linear projection, i.e., $$\tilde{q}_t = \mathcal{W}(\mathcal{N}(F'_t)),$$ (6)

$$k^g_t, v^g_t = \mathcal{W}(\mathcal{N}(G'_t)),$$

$$k^h_t, v^h_t = \mathcal{W}(\mathcal{N}(H'_t)).$$

Subsequently, the bi-directional cross-attention is devised to mine inter-slice reference information from the key and value features. Specifically, the query feature $\tilde{q}_t$, is used to calculate similarities with the bi-directional key features $$\{k^g_t, k^h_t\}.$$

Such similarities representing inter-slice correspondence are further used to aggregate reference information from $$\{v^g_t, v^h_t\},$$

yielding output features $$o^g_t$$

containing forward reference information and $$o^h_t$$

containing the backward reference information. This process can be formulated as $$o^g_t = v^g_t \times \sigma(k^g_t \times \tilde{q}_t),$$ (7)

$$o^h_t = v^h_t \times \sigma(k^h_t \times \tilde{q}_t),$$

in which × denotes the matrix multiplication and σ(·) denotes the softmax operation.

$$o^g_t \text{ and } o^h_t$$

are further channel-wisely concatenated to generate output features $\tilde{o}_t$ containing bi-directional reference information. Subsequently, $\tilde{o}_t$ is processed by layer normalization and concatenated with $\tilde{F}_t$, followed by the feed-forward network to generate the inter-slice context $\gamma_t$, i.e., $$\gamma_t = \mathcal{F}(F'_t \oplus \mathcal{N}(\tilde{o}_t)).$$ (8)

The BICE module is designed to effectively mine inter-slice correlations based on the bi-directional references {$g_t$, $h_t$}. By using the bi-directional cross-attention to mine and fuse forward and backward reference information, interview correlations are effectively explored, yielding representative inter-view context $\gamma_t$ for the compression of $r_t$.

The implementation details of the above-described framework in one specific implementation will now be described. Firstly, the reference software of the state-of-the-art video coding standard VVC (VTM-15.0, https://vcgit.hhi.fraunhofer.de/jvet/VVCSoftware VTM/-/tree/VTM-15.0) is adopted with the random access (RA) configuration for lossy compression. As for the residual coding, residues $r_0$ with respect to the first I frame within the GOP is compressed without reference slices and the BICE module is skipped. Meanwhile, residues $r_8$ with respect to the last P frame within the GOP is compressed conditioned on only the forward reference $x_0$, where $x_0$ and its replicas are sent into BICE to extract inter-slice context. In the BCM-Net, the feature extraction module is implemented by two residual blocks, and the residual blocks used in the feature extraction module, the BICE module and the SICE module are composed of two standard residual blocks proposed in ResNet [70]. Additionally, a two-stage context fusion strategy is used in the parameter estimation network ε(·). First, the intra-slice context $\kappa_t$ and inter-slice context $\gamma_t$ are channel-wisely concatenated and fused with residual blocks. Simultaneously, previously decoded sub-images $$r_t^{<i}$$

are processed by stacked convolution layers to extract the auto-regressive context. The fused context, along with the auto-regressive context, are further channel-wisely concatenated and fed into stacked convolution layers to produce probabilistic parameters $$\{\mu_t^i, \sigma_t^i, \pi_t^i\}$$

for sub-image $$r_t^i.$$

Moreover, the number of mixtures of the discrete logistic mixture model $p(\cdot)$ is set to 10, and the arithmetic encoder and the arithmetic decoded are implemented by torchac library[22].

The BCM-Net is implemented by PyTorch [71] and optimized by minimizing the negative log-likelihoods over training samples. The loss function can be formulated as $$\mathcal{L} = \mathbb{E}\left[-\sum_{m=0}^{M-1}\log\left(p(r_m^1|\kappa_m, \gamma_m) \cdot \prod_{i=2}^{4} p(r_m^i|r_m^{<i}, \kappa_m, \gamma_m)\right)\right], \quad (9)$$

in which M is the number of slices used in training. The Adam optimizer is used to optimize the BCM-Net with parameters $\beta_1$=0.9, $\beta_2$=0.999, and the batch size is set to 4. The learning rate is initialized as 0.0001 and decayed by a factor of 0.75 after every 20 epochs. Additionally, random horizontal flipping is used for data augmentation.

In the next section, the description is about performance of the method mentioned above is validated by experiments from the perspective of compression ratio. More specifically, datasets used in the experiments are first introduced, followed by the performance comparisons of the method against state-of-the-art 3D image lossless compression methods. Furthermore, ablation experiments are conducted to verify the effectiveness of different modules, and the model complexity as well as the encoding/decoding time are provided to demonstrate the feasibility of the proposed method.

The diverse acquisition techniques and applications result in the production of various 3D medical images with unique attributes. Therefore, three popular 3D medical image datasets covering common types of 3D medical images are used in the experiment to comprehensively evaluate the proposed method. As shown in Table I, 3D medical images from different datasets have quite different properties in terms of modality, resolution, bit-depth and types of organs, which enables thorough verification of the efficacy of the proposed method in different practical applications.

26

TABLE I

OVERVIEW OF 3D MEDICAL IMAGE DATASETS IN EXPERIMENTS.

| | MRNet [32] | MosMedData [66] | TRABIT [65] |
|---|---|---|---|
| Type | Knee MRI | Lung CT | Brain MRI |
| Training Samples | 3,390 | 125 | 70 |
| Test Samples | 360 | 45 | 30 |
| Slices per Sample | 17~61 | 33~72 | 176 |
| Bit Depth | 8 | 16 | 16 |
| Slice Resolution | 256 × 256 | 512 × 512 | 208 × 176 |

MRNet [32] is a large-scale knee MRI dataset, including 1370 knee 3D MRI images obtained from 1,201 patients. Each MRI image is partitioned into triple 2D slices along directions perpendicular to the sagittal plane, coronal plane, and axial plane, respectively. The 2D slices are then saved as 8-bit numpy arrays with a resolution of 256×256. In the experiment, the official training/test set division protocol [32] is adopted, i.e., 3,390 sets of slices are used for training and 360 sets of slices are used for test. For the lossy compression based on VVC, the GOP size is set to 16 and the quantization parameter (QP) is set to 37. Additionally, the first nine slices of training samples are used to train the BCM-Net, whereas all slices of test samples are involved in the evaluation of BCM-Net.

MosMedData [66] is an anonymized CT dataset and encompasses 172 high-quality human lung CT scans for COVID-19 diagnosis. The NIfTI format [72] is employed to store the Hounsfield unit (Hu) values of CT scans as 16-bit signed integers. MosMedData is divided into three non-overlapping subsets CT-2, CT-3 and CT-4, and the setting in [73] is followed to use the CT-2 subset including 125 scans for training and the CT-3 subset including 45 scans for testing. The CT scans are partitioned into slices along the direction perpendicular to the axial plane to generate 2D slices. Before lossy compression, CT scans are first converted into 16-bitunsigned integers by a shift operation to accommodate the lossy video codec, wherein the shift is encoded as head bits and transmitted to the decoding side. Herein, the GOP size is set to 16 and the QP is set to 17. Regarding the lossless compression, the first 25 slices of training samples are used to optimize the BCM-Net, while all slices of test samples are used in the evaluation.

TRABIT [65] is a brain MRI dataset provided by the TRABIT2019 imaging biomarkers competition. TRABIT consists of 70 brain MRI images for training and 30 brain MRI images for test, represented as 16-bit unsigned integers and stored in the NIfTI format. In the experiment, 3D MRI images are partitioned into 2D slices along the direction perpendicular to the axial plane. For the lossy compression of the proposed method, GOP size is set to 16 and QP is set to 0.96 slices of training samples are used to optimize the BCM-Net and all slices of test samples for evaluation.

In order to extensively verify the effectiveness of the proposed method, various compression methods for 3D medical images are adopted for comparisons. More specifically, traditional 2D lossless image compression methods, including PNG[74], JPEG-LS [16], JPEG-2000 [34], JPEG-2000 Part2 [17], FLIF [33] and JPEG-XL [19], are used to individually encode each slice of 3D medical images with default configurations. In addition, traditional 2D video coding methods, including HEVC [20], VVC [21] and FFV1 [75], and traditional 3D medical image compression methods JP3D [9] are employed with default configurations to encode 3D medical images as video sequences or volumetric data. The latest learned lossless compression methods, including L3C [22], ICEC [30] and aiWav-heavye [31], are also used as comparison methods.

The widely-used bit-per-pixel (bpp) is employed as the objective metric to evaluate compression efficiency. Besides, the compression ratio and bitrate saving ratio are further used to provide an intuitive demonstration of compression performance. The compression ratio is defined as the ratio between the size of the original 3D medical images and the size of the compressed size and can be formulated as $\eta = s_o/s_c$, where $s_o$ denotes the size of original 3D medical images and $s_c$ denotes the size of bitstreams yielded by lossless compression methods. Meanwhile, the bitrate savings ratio is defined as the bit consumption savings of a given compression method relative to the anchor (which is set to FLIF[33] in all experiments), i.e., $\theta = (\beta - \alpha)/\beta$, where $\alpha$ denotes the bit consumption of the given compression method and $\beta$ denotes the bit consumption of the anchor.

Turning to the performance comparisons, Table II in FIG. 11 shows the performance comparisons on the MRNetdataset [32], where the performance of ICEC [30] and aiWave [31] are adopted from [31]. For the Axial subset, the proposed method costs an average of 4.41 bpp to compress 3D MRI images, achieving a compression ratio of 1.814. Comparatively, ICEC [30] compresses 3D MRI images with an average cost of 4.64 bpp, resulting in a compression ratio of 1.724, and aiWave [31] costs an average of 4.55 bpp with a compression ratio of 1.758. Compared with ICEC [30] and aiWave [31], the proposed method achieves further 4.9% and 3.1% bit-saving, respectively. On the Coronal subset, the proposed method spends an average of 3.63 bpp with a compression ratio of 2.204, while aiWave spends an average of 3.80 bpp with a compression ratio of 2.105. Compared with aiWave[31], the proposed method further saves 4.5% bit consumption. Moreover, consistent observations are obtained on the Sagittal subset, where the proposed method achieves 0.4% bit savings compared to aiWave [31].

To evaluate the performance of the proposed method on 3D medical images with high quality and high bit-depth, quantitative experiments are conducted on the MosMedData dataset, and the results are shown in Table III. In this experiment, the performance of aiWave [31] is adopted from their proposal[73]. It can be observed that the proposed method out performs other comparative methods, achieving an average bit cost of 4.71 bpp and a compression ratio of 3.397. JPEG-XL [19] delivers the best performance among traditional compression methods with an average cost of 4.72 bpp. Meanwhile, the most advanced learned method aiWave [31] requires 4.91 bpp to compress 3D medical images of MosMedData and achieves a compression ratio of 3.259. Compared to aiWave [31], the proposed method achieves an additional 4.1% bit saving.

TABLE III

PERFORMANCE COMPARISONS
ON THE MOSMEDDATA DATASET.

| Methods | Bpp ↓ | Compression Ratio ↑ | Bitrate Saving Ratio ↑ |
|---|---|---|---|
| PNG [74] | 7.05 | 2.270 | −43.8% |
| JPEG-LS [16] | 4.97 | 3.219 | −1.3% |
| JPEG-2000 [34] | 5.27 | 3.036 | −7.6% |
| JP3D [9] | 5.38 | 2.974 | −9.8% |
| JPEG-2000-Part2 [17] | 5.28 | 3.030 | −7.7% |
| FLIF [33] | 4.90 | 3.265 | 0.0% |
| JPEG-XL [19] | 4.72 | 3.390 | 3.7% |
| HEVC-RExt-Intra [20] | 5.15 | 3.107 | −5.0% |

TABLE III-continued

PERFORMANCE COMPARISONS
ON THE MOSMEDDATA DATASET.

| Methods | Bpp ↓ | Compression Ratio ↑ | Bitrate Saving Ratio ↑ |
|---|---|---|---|
| HEVC-RExt [20] | 5.12 | 3.125 | −4.4% |
| FFV1 [75] | 5.00 | 3.200 | −2.0% |
| VVC-Intra [21] | 5.34 | 2.996 | −9.0% |
| VVC [21] | 5.30 | 3.019 | −8.2% |
| aiWave [31] | 4.91 | 3.259 | −0.2% |
| Proposed | 4.71 | 3.397 | 3.9% |

Table IV presents the performance comparison on TRA-BIT, where the performance results of aiWave [31] as reported in their proposal [73] are adopted. It can be observed that the proposed method achieves state-of-the-art performance on the TRABIT dataset. More specifically, the proposed method delivers an average bit consumption of 1.91 bpp and a compression ratio of 8.377, which is comparable to the state-of-the-art comparison method aiWave [31]. Additionally, the proposed method achieves significant bit savings compared to other methods.

TABLE IV

PERFORMANCE COMPARISONS ON THE TRABIT DATASET.

| Methods | Bpp ↓ | Compression Ratio ↑ | Bitrate Saving Ratio ↑ |
|---|---|---|---|
| PNG [74] | 3.08 | 5.195 | −40.8% |
| JPEG-LS [16] | 2.22 | 7.207 | −1.4% |
| JPEG-2000 [34] | 2.58 | 6.202 | −17.9% |
| JP3D [9] | 2.56 | 6.250 | −17.0% |
| JPEG-2000-Part2 [17] | 2.62 | 6.107 | −19.4% |
| FLIF [33] | 2.19 | 7.306 | 0.0% |
| JPEG-XL [19] | 2.10 | 7.619 | 4.1% |
| HEVC-RExt-Intra [20] | 2.28 | 7.018 | −4.2% |
| HEVC-RExt [20] | 2.14 | 7.477 | 2.1% |
| FFV1 [75] | 2.22 | 7.207 | −1.4% |
| VVC-Intra [21] | 2.65 | 6.038 | −21.0% |
| VVC [21] | 2.39 | 6.695 | −9.1% |
| aiWave [31] | 1.91 | 8.377 | 12.8% |
| Proposed | 1.91 | 8.377 | 12.8% |

In the next part of the description, ablation studies are conducted on the BICE module, the SICE module and the lossy-to-lossless framework to verify their effectiveness. The BICE module is proposed to effectively exploit inter-slice correlations from bi-directional references $\{g_t, h_t\}$ to generate inter-slice context $\gamma_t$. In order to verify the contribution of $\gamma_t$, the BICE module is removed in ablation studies; consequently, the lossless compression of residues $r_t$ no longer conditions on the inter-slice context $\gamma_t$. The results are shown in Table V and denoted as "w/o BICE module". It can be observed that, after removing the BICE module, the bit consumption rises from 4.41 to 4.43 on the Axial subset of MRNet, i.e., 0.5% increase of bit consumption, and the compression ratio witnesses a decline from 1.814 to 1.806. Consistent trends are observed on the Coronal and Sagittal subsets of MRNet, with the bit consumption increment by 1.1% and 0.2%, respectively. This is because after removing the BICE module, the BCM-Net cannot use the bilateral correlations between slices to improve the probability estimation, resulting in a deterioration of the compression performance.

TABLE V

ABLATION STUDIES ON THE MRNET DATASET.

| | Axial | | | Coronal | | | Sagittal | | |
|---|---|---|---|---|---|---|---|---|---|
| | Bpp ↓ | Compression Ratio ↑ | Bitrate Saving Ratio ↑ | Bpp ↓ | Compression Ratio ↑ | Bitrate Saving Ratio ↑ | Bpp ↓ | Compression Ratio ↑ | Bitrate Saving Ratio ↑ |
| w/o BICE module | 4.43 | 1.806 | 8.9% | 3.67 | 2.180 | 8.3% | 4.82 | 1.660 | 6.5% |
| w/o SICE module | 4.48 | 1.786 | 7.9% | 3.73 | 2.145 | 6.6% | 4.88 | 1.639 | 5.5% |
| w/o Lossy | 4.98 | 1.606 | −2.4% | 4.09 | 1.956 | −2.3% | 5.05 | 1.584 | 2.1% |
| Proposed | 4.41 | 1.814 | 9.2% | 3.63 | 2.204 | 9.3% | 4.81 | 1.663 | 6.9% |

The SICE module is designed to efficiently explore intra-slice correlations from lossy reconstruction $\tilde{x}_t$ based on anatomical symmetry, and generate intra-slice context $\kappa_t$ to provide prior information for the lossless compression of residues $r_t$. In order to verify the effectiveness of $\kappa_t$, the SICE module is replaced by residual blocks to derive vanilla intra-slice context $$\kappa'_t$$

without the utilization of anatomical symmetry. The results are shown in Table V, denoted as "w/o SICE module". It can be observed that the compression performance suffers a drop after replacing the SICE module with residual blocks. Specifically, on the Axial subset of MRNet, the bit consumption increases from 4.41 to 4.48, i.e., 1.6% increase of bit consumption, and the compression ratio also decreases from 1.814 to 1.786. On the Coronal and Sagittal subsets of MRNet, the bit consumption increases by 2.8% and 1.5%, respectively. Correspondingly, the compression ratio decreases from 2.204 to 2.145 on the Coronal subset and from 1.663 to 1.639 on the Sagittal subset. These adverse outcomes stem from the incapacity of BCM-Net to effectively mine intra-slice correlations without the SICE module, leading to inadequate intra-slice prior information. The absence of sufficient prior information further affects the efficiency of residual coding.

The proposed method employs a lossy-to-lossless framework for efficient compression, wherein lossy compression is first leveraged to compress original slices and lossless compression is then used to effectively encode residues between original slices and lossy reconstructions. To validate the efficacy of such a lossy-to-lossless framework in 3D medical image compression, ablation experiments are conducted by removing the lossy compression, such that the original slices are straightforwardly compressed in a lossless manner. Furthermore, hyper-priors extracted from the current slice xt are compressed, and substituted for the lossy reconstruction $\tilde{x}_t$ to provide intra-slice context. Specifically, the analysis transform [76] is used to extract latents from input slices. Then, the scalar quantization, the factorized entropy model [76] and the arithmetic coding are used to encode the latent representations into bitstreams. The hyper-priors are generated from the decoded latents through the synthesis transform [76]. Additionally, the number of channels of the latents is set to 5 and that of the hyper-priors is set to 64, which is identical to the settings in L3C [22]. The corresponding results are shown in Table V and denoted as "w/o Lossy". It can be observed that, after disabling the lossy-to-lossless paradigm, the bit consumption increases from 4.41 bpp to 4.98 bpp on the Axial subset, which represents an extra 12.9% bit cost and a deterioration in compression ratio from 1.814 to 1.606. Similarly, ablation experiments on the Coronal and Sagittal subsets exhibit an increase of 12.7% and 5.0% bit consumption, respectively. This is because the lossless compression network has to estimate distributions of original signals instead of relatively compact residues after removing the lossy compression, causing a degradation in the coding performance.

B-frames coding structure: B-frames coding structure [60] is adopted in the proposed method to provide bi-directional references for the compression in both lossy layer and residual layer. To validate the effectiveness of B-frames coding, a variant denoted as "P-frames coding with VVC" is introduced. In this variant, VTM with the default LDP configuration is used for lossy coding, and the BICE module utilizes two forward references as inputs. The results on the Coronal subset of MRNet are presented in Table VI. It can be observed that replacing B-frames coding with P-frames coding leads to a 1.1% increase in bitrate consumption. This is because the proposed method is unable to leverage the bi-directional inter-slice correlations under the P-frames coding configurations. These results further demonstrate the effectiveness of B-frame coding in the lossless compression of 3D medical images.

TABLE VI

PERFORMANCE COMPARISONS ACROSS DIFFERENT CODING STRUCTURES AND LOSSY LAYER CODECS ON THE CORONAL SUBSET OF MRNET.

| | Bpp ↓ | Compression Ratio ↑ | Bitrate Saving Ratio ↑ | #Params |
|---|---|---|---|---|
| P-frames coding with VVC | 3.67 | 2.180 | 8.39% | 12.5M |
| P-frames coding with DCVC-DC | 3.66 | 2.186 | 8.53% | 63.3M |
| Proposed | 3.63 | 2.204 | 9.3% | 12.5M |

In the proposed method, VTM-15.0 is used to achieve lossy compression of 3D medical images. To assess the impact of different lossy codecs on compression performance, the lossless coding performance when using VTM-15.0 is compared with the state-of-the-art neural video codec DCVC-DC [52] as the lossy layer. As shown in Table VI, the P-frames coding variant with DCVC-DC [52] as the lossy layer exhibits a slight improvement over the variant using VVC as the lossy layer. The improvement can be attributed to the enhanced lossy coding performance of DCVC-DC [52]. Moreover, these results show the scalability of the proposed method, that is, the proposed method can seamlessly integrate the state-of-the-art video codec.

The proposed method is compared with the highly efficient traditional compression method 3D-MRP [11] on two accessible 3D medical images used by 3D-MRP [11], namely CT Head and MR Brain. Table VII shows the comparison of bits consumption, encoding time and decoding time, where the performance of 3D-MRP [11] is adopted from their published paper. It can be observed that the proposed method does not surpass 3D-MRP [11] in terms of bit consumption. This may be because the distributions of the two test 3D medical images are quite different from the training data used by the proposed method. This domain gap further hampers the modeling of signals by the proposed method. Meanwhile, it is worth mentioning that the encoding complexity of the proposed method is significantly lower than that of 3D-MRP [11]. This is because 3D-MRPemploys computationally expensive online optimization during the encoding process, while the proposed method does not require any optimization during the encoding process. The encoding time saving of the proposed method compared to 3D-MRP [11] indicates the feasibility of the proposed method in real-world applications.

TABLE VII

PERFORMANCE COMPARISON ON THE
CT__HEAD AND MR__BRAIN IMAGES.

| Methods | CT__Head | | | MR__Brain | | |
|---|---|---|---|---|---|---|
| | Bpp | Enc-time | Dec-time | Bpp | Enc-time | Dec-time |
| 3D-MRP [11] | 4.108 | 17451.75 s | 3.02 s | 6.233 | 17847.00 s | 3.47 s |
| Proposed | 5.779 | 2573.34 s | 6.95 s | 7.773 | 3264.30 s | 7.32 s |

Table VIII illustrates the model size and encoding/decoding time of the proposed method and other comparison methods on the Coronal subset of MRNet [32]. For the ICEC [30] and aiWave [31], the model sizes reported in their corresponding papers have been employed. Comparison methods and the proposed method are evaluated on a PC equipped with Intel i7-13700KF CPU and NVIDIA RTX 4090 GPU. Specifically, benefiting from the compression of residues instead of original signals, the model size of the proposed method, i.e., the model size of BCM-Net, is 29.4% smaller than that of ICEC [30] and 97.5% smaller than aiWave [31]. It is worth mentioning that the reduction in model size is partly due to the incorporation of the lossy layer, that is, the proposed BCM-Net only needs to model the residues based on the lossy reconstructions. This task is comparatively easier than modeling the original signals (as done in ICEC [30] and aiWave [31]). Consequently, the need for a large amount of parameters is eliminated. Additionally, the model size of the P-frames variant with neural codec DCVC-DC [52] is reported as the lossy layer. The parameter amount of this variant is 63.3M, of which the parameter amount of the lossy layer (i.e., DCVC-DC [52]) is 50.8M, and the parameter amount of BCM-Net used for residual lossless coding is 12.5M. The model size of this variant increases by 45.6M as compared to ICEC [30] and is smaller than that of aiWave [31].

As for the coding runtime 3, the encoding time of the proposed method is less than VVC [21], and longer than other traditional methods, which is primarily due to the lossy compression phase. This issue can also be mitigated by employing the optimized implementation of VVC [77] and multithreading coding techniques [78].

One can see that in summary, the proposed method described above in accordance with an exemplary embodiment of the invention is a bilateral context modeling mechanism for residual coding in 3D medical image compression, in which the bilateral correlations in 3D medical images are efficiently explored to yield representative priors. In specific, the SICE module is devised to capture bilateral correlations from lossy reconstructions based on the principle of anatomical symmetry, generating effective intra-slice context for the compression of residues. Additionally, in order to exploit bilateral correlations between slices as effective priors, the BICE module is proposed to mine correlations based on bi-directional references and generate representative inter-slice context. With both the intra-slice and inter-slice context, the designed lossless compression network can accurately estimate the distributions of residues, leading to more compact bitstreams. Experimental results on prevailing 3D medical image datasets demonstrate that the proposed method achieves promising compression performance and outperforms state-of-the-art methods.

Figure 12A:
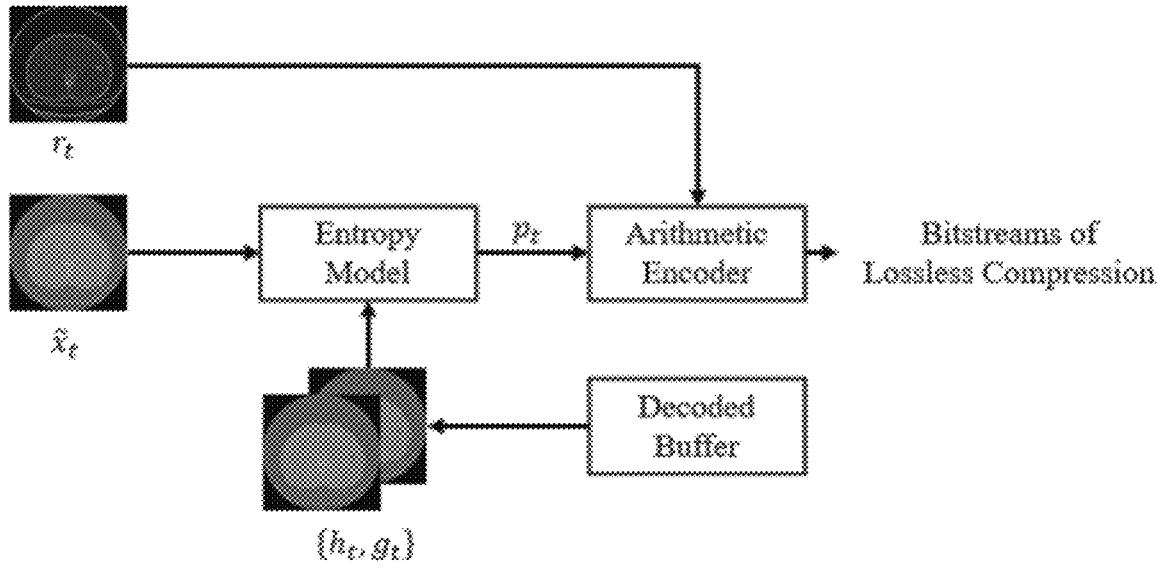
FIG. 12a is a schematic diagram illustrating an encoder of lossless according to a further embodiment of the invention.
Figure 12B:
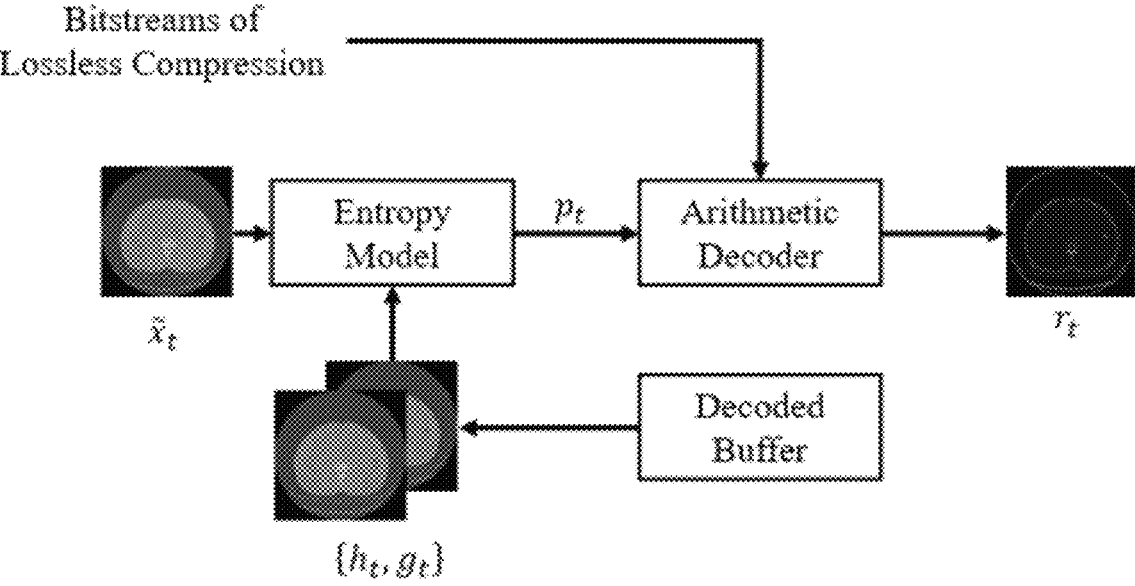
FIG. 12b is a schematic diagram illustrating a decoder of lossless according to a further embodiment of the invention.

FIG. 12$a$ illustrates an encoder of lossless compression and its operation according to another embodiment. As shown in FIG. 12$a$, the encoder of lossless compression includes an entropy model arranged to estimate probability distributions of residuals and an arithmetic encoder arranged to losslessly compress residuals based on the estimated probability distributions. In some embodiments, the residual set $R=\{r_1, r_2, \ldots, r_N\}$ are sequentially compressed according to the example hierarchical-B-frame coding structure shown in FIG. 4. For the current residuals $r_t \in R$, the forward decoded slice $h_t$ and the backward decoded slice $g_t$ are assigned as the bi-directional references, together with the lossy reconstruction $\tilde{x}_t$ to provide conditional priors for $r_t$. The entropy model is designed to estimate the probability $p_t$ of $r_t$ based on the condition priors, followed by the arithmetic encoder to compress $r_t$ to compact bitstreams according to $p_t$.

FIG. 12$b$ illustrates a decoder of lossless compression and its operation according to one embodiment of the invention. As shown in FIG. 12$b$, the entropy model is used to provide probability $p_t$ and the arithmetic decoder is used to decompress $r_t$ from the lossless bitstreams based on $p_t$.

Figure 13:
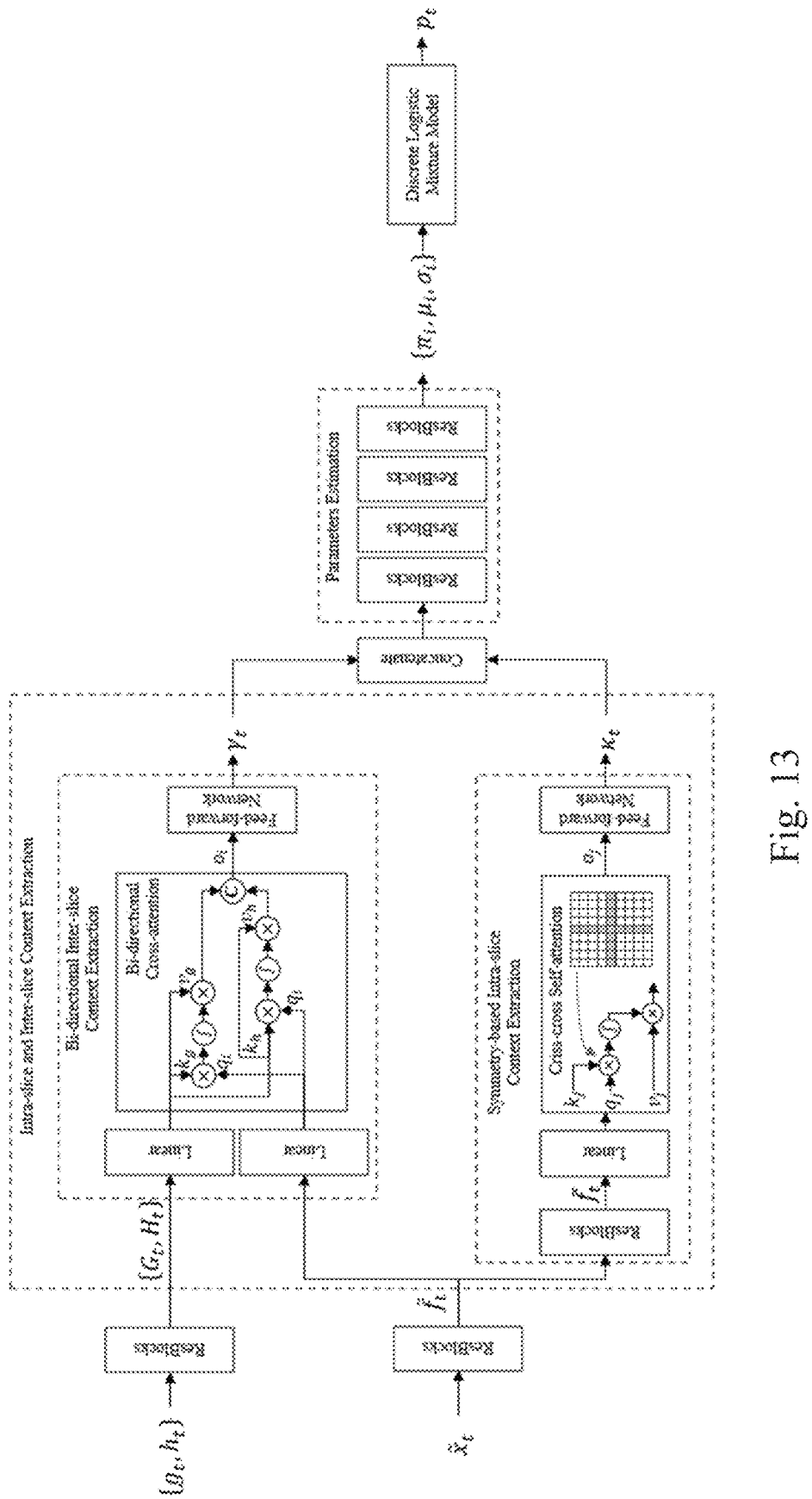
FIG. 13 is a schematic diagram illustrating an entropy model in the encoder of lossless compression and the decoder of lossless compression according to one embodiment of the invention.

FIG. 13 illustrates an entropy model in the encoder of lossless compression of FIG. 12$a$ and the decoder of lossless compression in FIG. 12$b$ according to one embodiment of the invention. As shown in FIG. 13, in this embodiment, the entropy model takes the bi-directional reference slice $\{h_t, g_t\}$ and the lossy reconstruction slice $\tilde{x}_t$ as inputs and estimates the probability distribution $p_t$, including the intra-slice and inter-slice context extraction module, the parameter estimation module, and the discrete logistic mixture model. In this embodiment, in the intra-slice and inter-slice context extraction module, reference features $\{H_t, G_t\}$ and lossy feature $\tilde{f}_t$ are extracted from $\{h_t, g_t\}$ and $\tilde{x}_t$ using residual blocks, respectively. Then, the bi-directional inter-slice context extraction (BICG) module is devised to explore inter-slice correlations from $\{H_t, G_t\}$ to generate inter-slice context $\gamma_t$, and the symmetry-based intra-slice context extraction (SICG) module is devised to explore intra-slice correlations from $\tilde{f}_t$ to generate intra-slice context $\kappa_t$. Specifically, in the BICG module in one embodiment, the forward reference feature $H_t$ is processed by a linear layer to generate features $\{k_h, v_h\}$, and similar process is also applied to $G_t$ to generate features $\{k_g, v_g\}$. This process can be formulated as follows:

$$k_h, v_h = \text{Linear}_h(H_t), \tag{10}$$

$$k_g, v_g = \text{Linear}_g(G_t),$$

where $\text{Linear}(\cdot)(\cdot)$ denotes the linear layer. Besides, a linear layer is applied to the lossy feature $\tilde{f}_t$ to generate feature $q_i$ to query inter-slice correlations, i.e., $$q_i = \text{Linear}_i(\tilde{f}_t). \tag{11}$$

Then, the bi-directional cross-attention is designed to explore forward inter-slice correlations provided by $G_t$ and backward inter-slice correlations provided by $H_t$. This process can be formulated as follows:

$$o_g = v_g \times \sigma(k_g \times q_i), \tag{12}$$

$$o_h = v_h \times \sigma(k_h \times q_i),$$

where $\sigma(\cdot)$ denotes the SoftMax operation, $o_g$ denotes the forward context containing forward reference information and $o_h$ denotes the context containing backward reference information. Due to the bi-directional cross-attention, the BICG module can exploit both local and global inter-slice correlations and attain representative reference information. Then, $o_g$ and $o_h$ are fused and processed by the feed-forward network, yielding inter-slice context $\gamma_t$, i.e., $$\gamma_t = FFN(o_g \oplus o_h). \tag{13}$$

where $\oplus$ denotes the channel-wise concatenation and $FFN(\cdot)$ denotes the feed-forward network.

In one embodiment, as symmetry may be present in medical images, the SICG module is designed to efficiently capture correlations between pixels of $\tilde{f}_t$ along the symmetrical axis to generate the intra-slice context $\kappa_t$. Specifically, in one embodiment, to mine the local correlations stemming from the local anatomical symmetry, a residual block is first applied to $\tilde{f}_t$ to aggregate neighborhood information, yielding intra-slice features $\hat{f}_t$. Subsequently, triplet $\{q_j, k_j, v_j\}$ are derived by linear layers, i.e., $$q_j, k_j, v_j = \text{Linear}_j(\bar{f}_t). \tag{14}$$

Following that, the criss-cross self-attention module is then designed to mine the long-range correlations originating from the global anatomical symmetry. Based on the criss-cross query pattern shown in FIG. 13, correlations of pixels of $q_j$ is acquired by calculating similarity along the directions perpendicular to two axes of symmetry, i.e., the horizontal and vertical symmetry axes. In this way, the global anatomical symmetry is involved to facilitate the exploration of correlations within $f_t$ and generate more representative intra-slice context. Finally, the outputs $o_j$ containing local and global correspondence information is fed into the feed-forward network to generate the intra-slice context $\kappa_t$.

In one embodiment, the probability distribution $p_t$ is conditioned on the inter-slice context $\gamma_t$ and the intra-slice context $\kappa_t$ and parametrically modeled by the discrete logistic mixture model, i.e., $$p_t(r_t | \gamma_t, \kappa_t) = DLMM(\pi_i, \mu_i, \sigma_i), \tag{15}$$

where $DLMM(\cdot)$ denotes the discrete logistic mixture model and $\{\pi_i, \mu_i, \sigma_i\}$ are the parameters estimated based on $\{\gamma_t, \kappa_t\}$. Specifically, the intra-slice context $\kappa_t$ and the inter-slice context $\gamma_t$ are channel-wisely concatenated and processed by stacked residual blocks, yielding parameters $\{\mu_i, \mu_i, \sigma_i\}$, i.e., $$\pi_i, \mu_i, \sigma_i = ResBlocks(\kappa_t \oplus \gamma_t), \tag{16}$$

where $ResBlocks(\cdot)$ denotes the stacked residual blocks. Following that, the discrete logistic mixture model is used to calculate the probability distribution $p_i$, i.e., $$p_i = \sum_{k=1}^{K} \pi_i^k \left( \text{Sigmoid}\left( \frac{r_i + \frac{1}{2} - \mu_i^k}{\sigma_i^k} \right) - \text{Sigmoid}\left( \frac{r_i - \frac{1}{2} - \mu_i^k}{\sigma_i^k} \right) \right), \tag{17}$$

where $\text{Sigmoid}(\cdot)$ denotes the sigmoid operation, $K$ denotes the number of mixtures.

Some embodiments of the invention provide a lossless compression method for 3D medical images, in which inter-slice and/or intra-slice correlations are exploited to reduce the redundancy of 3D medical images. Some embodiments of the invention provide a lossy-then-lossless compression pipeline, in which smooth contents of 3D medical images are effectively compressed by the lossy encoder and the residuals containing intricate details are handled by the lossless encoder. Some embodiments of the invention adopt a hierarchical-B coding structure to provide bi-directional references for the compression of 3D medical image and/or use advanced video coding technologies to reduce intra-slice and inter-slice redundancy in the lossy compression phase. Some embodiments of the invention provide a learning-based lossless compression network, which may include an entropy model to accurately estimate the probability of residuals by exploring intra-slice and inter-slice context as priors, and an arithmetic encoder to efficiently compress residuals based on the estimated probability. Some embodiments of the invention provide a bi-directional inter-slice context extraction module to exploit inter-slice context from bi-directional references, in which a bi-directional cross-attention mechanism is devised to capture global inter-slice correlations from the forward and backward references. Some embodiments of the invention provide a symmetry-based intra-slice context extraction module to exploit intra-slice context, in which correlations is exploited based on the local and global anatomical symmetry to generate representative intra-slice context for the lossless compression.

Some embodiments of the invention may include one or more of the following features:

1. The 3D medical image can be partitioned into slices for processing.

In one example, the 3D medical images may be partitioned along a specified axis to generate the slices.

In one example, the partitioned axis is specified as the axis perpendicular to the transverse plane.

In one example, the partitioned axis is specified as the axis perpendicular to the sagittal plane.

In one example, the partitioned axis is specified as the axis perpendicular to the coronal plane.

In one example, the usage of the partitioned axis is signaled with flag(s).

In one example, the axis perpendicular to the transverse plane is the default partitioned axis.

2. The slices can be encoded to bitstreams by the lossy compression, and the bitstreams can be decoded to lossy reconstructed slices.

In one example, the lossy compression may include an encoder and a decoder, and may be implemented using video codec.

In one example, the lossy compression provided by VVC may be used.

In one example, the lossy compression provided by HEVC may be used.

In one example, the lossy compression provided by H.264/MPEG-4 AVC may be used.

In one example, the lossy compression provided by AVS may be used.

In one example, the lossy compression may be a type of video/image codec.

In one example, hierarchical-B coding structure and bi-directional inter-prediction may be used.

In one example, whether to use the bi-directional inter-prediction is indicated with flag(s).

3. Residuals between original slices and lossy reconstructed slices are calculated and compressed to bitstreams by the encoder of lossless compression. The bitstreams can be decompressed to decoded residuals by the decoder of lossless compression.

In one example, the encoder of lossless compression may include an entropy model and an entropy encoder.

In one example, the entropy model may be a learning-based entropy model.

In one example, the entropy encoder may bean arithmetic encoder.

In one example, the decoder of lossless compression may include an/the entropy model and an/the entropy decoder.

In one example, the entropy model may be a/the learning-based entropy model.

In one example, the entropy decoder may be a/the arithmetic decoder.

4. The learning-based entropy model can be used to estimate probability distributions of residuals based on the lossy reconstructed slices and the bi-directional references.

In one example, the learning-based entropy model may include an intra-slice and inter-slice context extraction module, a parameters estimation module, and a parametrical probability model.

In one example, the intra-slice and inter-slice context extraction module may take the lossy reconstructed slices, the forward references, the backward references as input and generate context.

In one example, the parameters estimation module may leverage the context to generate parameters for the parametrical probability model.

In one example, the parameters estimation module may be formed by a set of stacked residual blocks.

In one example, the parametrical probability model may generate probability distributions of residuals based on the estimated parameters.

In one example, the parametrical probability model may be a discrete logistic mixture model.

5. The intra-slice and inter-slice context extraction module may include an intra-slice context extraction module, an inter-slice context extraction module, and a context fusion operation.

In one example, the lossy reconstructed slices may be processed by the stacked residual blocks to generate lossy features.

In one example, the forward reference and the backward reference can be processed by the stacked residual blocks to generate forward reference features and backward reference features.

In one example, the lossy features may be processed by the intra-slice context extraction module to generate the intra-slice context.

In one example, the intra-slice context extraction module may be a symmetry-based intra-slice context extraction module.

In one example, the forward reference features and backward reference features may be processed by the inter-slice context extraction module to generate the inter-slice context.

In one example, the inter-slice context extraction module may be a bi-directional inter-slice context extraction module.

In one example, the intra-slice context and the inter-slice context may be fused by the context fusion operation to generate context as priors for the residuals.

In one example, the context fusion operation may be channel-wise concatenation.

6. The symmetry-based intra-slice context extraction module may include the local correlation exploration and the global correlation exploration.

In one example, the local correlation exploration may be implemented by stacked residual blocks.

In one example, the global correlation exploration may be implemented by a criss-cross self-attention module.

In one example, the intra-slice correlations may be acquired by calculating similarity along the directions perpendicular to two axes of symmetry, i.e., the horizontal and vertical symmetry axis.

In one example, the criss-cross query pattern may be used for the similarity calculation.

7. The bi-directional inter-slice context extraction module may include linear layer(s), a bi-directional cross-attention, and a feed-forward network.

In one example, the forward reference features may be processed by the linear layer to generate forward key features and forward value features.

In one example, the backward reference features may be processed by the linear layer to generate backward key features and backward value features.

In one example, the lossy features may be processed by the linear layer to generate query features.

In one example, the query features, the forward key features, the forward value features, the backward key features and the backward value features may be processed by the bi-directional cross-attention to generate inter-slice contextual features.

In one example, the query features and the forward key features may be multiplied to generate forward attention map, followed by the multiplication of the forward value features and the forward attention map to generate forward contextual features.

In one example, the query features and the backward key features may be multiplied to generate backward attention map, followed by the multiplication of the backward value features and the backward attention map to generate backward contextual features.

In one example, the forward contextual features and the backward contextual features may be channel-wisely concatenated to generate inter-slice contextual features.

In one example, the inter-slice contextual features may be processed by the feed-forward network to generate inter-slice context.

Some embodiments of the invention may provide one or more of the following example advantages. Some embodiments of the invention may provide one or more additional advantages or one or more alternative advantages. For example, some embodiments provide an efficient lossless 3D medical image compression framework, including the lossy-then-lossless compression pipeline, the advanced lossy compression based on video coding, and the learning-based lossless compression. For example, in some embodiments, with the lossy-then-lossless compression pipeline, the smooth contents of 3D medical image are effectively encoded by the lossy compression, and the residuals containing intricate details are further handled by the lossless compression. For example, in some embodiments, the hierarchical-B coding structure is adopted to provide bi-directional references for the compression of 3D medical image, and one or more advanced video coding technologies are used in reducing intra-slice and inter-slice redundancy in the lossy compression phase. For example, in some embodiments, in the lossless compression network, both intra-slice and inter-slice correlations are exploited to improve compression. For example, in some embodiments, a bi-directional inter-slice context extraction module is designed to exploit inter-slice context from bi-directional references, and a symmetry-based intra-slice context extraction module is designed to effectively exploit intra-slice context based on the local and global anatomical symmetry. For example, in some embodiments, with the prior information on the intra-slice and inter-slice context, the lossless compression network can accurately estimate probability distributions of residuals and achieve good compression efficiency.

Various method embodiments of the invention may be implemented using system implemented with hardware and/or software.

Figure 14:
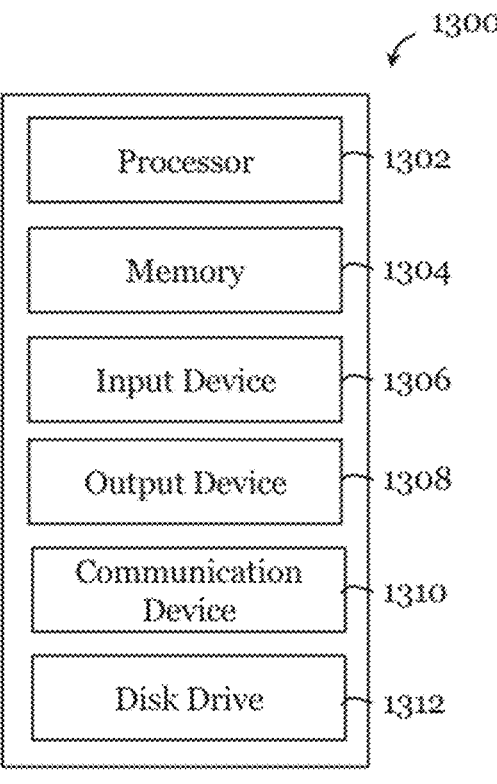
FIG. 14 is a schematic diagram illustrating a data processing system in some embodiments of the invention.

FIG. 14 shows a data processing system 1300 in some embodiments of the invention. The data processing system 1300 may be used as at least part of the system 10, at least part of the system 20, at least part of the encoder 500, at least part of the decoder 600, etc. The data processing system 1300 may be used to perform or to facilitate performing of one or more method embodiments of the invention. The data processing system 1300 may be used as at least part of an encoder, a decoder, a codec, etc.

The data processing system 1300 generally comprises suitable components necessary to receive, store, and execute appropriate computer instructions, data, commands, and/or codes. The main components of the data processing system 1300 are a processor 1302 and a memory (storage) 1304. The processor 1302 may include one or more: CPU(s), MCU(s), GPU(s), logic circuit(s), Raspberry Pi chip(s), digital signal processor(s) (DSP), application-specific integrated circuit(s) (ASIC), field-programmable gate array(s) (FPGA), or any other digital or analog circuitry/circuitries configured to interpret and/or to execute program instructions and/or to process signals and/or information and/or data. The memory 1304 may include one or more volatile memory (such as RAM, DRAM, SRAM, etc.), one or more non-volatile memory (such as ROM, PROM, EPROM, EEPROM, FRAM, MRAM, FLASH, SSD, NAND, NVDIMM, etc.), or any of their combinations. Appropriate computer instructions, commands, codes, information and/or data may be stored in the memory 1304. Computer instructions for executing or facilitating executing the method embodiments of the invention may be stored in the memory 1304. The processor 1302 and memory (storage) 1304 may be integrated or separated (and operably connected).

Optionally, the data processing system 1300 further includes one or more input devices 1306. Example of such input device 1306 include: keyboard, mouse, stylus, image scanner, microphone, tactile/touch input device (e.g., touch sensitive screen), image/video input device (e.g., camera), etc. The input device 1306 may be used to receive user input. Optionally, the data processing system 1300 further includes one or more output devices 1308. Example of such output device 1308 include: display (e.g., monitor, screen, projector, etc.), speaker, headphone, earphone, printer, additive manufacturing machine (e.g., 3D printer), etc. The display may include an LCD display, a LED/OLED display, or other suitable display, which may or may not be touch sensitive. The output device 1308, e.g., the display, may be used to display the 3D medical image, images of the original slices, images of the reconstructed slices, images of the residual slices, etc. The data processing system 1300 may further include one or more disk drives 1312 which may include one or more of: solid state drive, hard disk drive, optical drive, flash drive, magnetic tape drive, etc. A suitable operating system may be installed in the data processing system 1300, e.g., on the disk drive 1312 or in the memory 1304. The memory 1304 and the disk drive 1312 may be operated by the processor 1302. Optionally, the data processing system 1300 also includes a communication device 1310 for establishing one or more communication links (not shown) with one or more other computing devices, such as servers, personal computers, terminals, tablets, phones, watches, IoT devices, or other wireless computing devices. The communication device 1310 may include one or more of: a modem, a Network Interface Card (NIC), an integrated network interface, an NFC transceiver, a ZigBee transceiver, a Wi-Fi transceiver, a Bluetooth® transceiver, a radio frequency transceiver, a cellular (2G, 3G, 4G, 5G, above 5G, etc.) transceiver, an optical port, an infrared port, a USB connection, or other wired or wireless communication interfaces. Transceiver may be implemented by one or more devices (integrated transmitter(s) and receiver(s), separate transmitter(s) and receiver(s), etc.). The communication link(s) may be wired or wireless for communicating commands, instructions, information and/or data. In one example, the processor 1302, the memory 1304 (optionally the input device(s) 1306, the output device(s) 1308, the communication device(s)

1310 and the disk drive(s) 1312, if present) are connected with each other, directly or indirectly, through a bus, a Peripheral Component Interconnect (PCI), such as PCI Express, a Universal Serial Bus (USB), an optical bus, or other like bus structure. In one embodiment, at least some of these components may be connected wirelessly, e.g., through a network, such as the Internet or a cloud computing network.

A person skilled in the art would appreciate that the data processing system 1300 in FIG. 13 is merely an example and that the data processing system 1300 can, in other embodiments, have different configurations (e.g., include additional components, has fewer components, etc.).

Although not required, one or more embodiments described with reference to the Figures can be implemented as an application programming interface (API) or as a series of libraries for use by a developer or can be included within another software application, such as a terminal or computer operating system or a portable computing device operating system. In one or more embodiments, as program modules include routines, programs, objects, components, and data files that assist in the performance of particular functions, the skilled person will understand that the functionality of the software application may be distributed across a number of routines, objects, and/or components to achieve the same functionality desired herein.

It will also be appreciated that where the methods and systems of the invention are either wholly implemented by computing system or partly implemented by computing systems then any appropriate computing system architecture may be utilized. This will include stand-alone computers, network computers, dedicated or non-dedicated hardware devices. Where the terms "computing system" and "computing device" are used, these terms are intended to include (but not limited to) any appropriate arrangement of computer or information processing hardware capable of implementing the function described.

The exemplary embodiments are thus fully described. Although the description referred to particular embodiments, it will be clear to one skilled in the art that the invention may be practiced with variation of these specific details. Hence this invention should not be construed as limited to the embodiments set forth herein.

While the embodiments have been illustrated and described in detail in the drawings and foregoing description, the same is to be considered as illustrative and not restrictive in character, it being understood that only exemplary embodiments have been shown and described and do not limit the scope of the invention in any manner. It can be appreciated that any of the features described herein may be used with any embodiment. The illustrative embodiments are not exclusive of each other or of other embodiments not recited herein. Accordingly, the invention also provides embodiments that comprise combinations of one or more of the illustrative embodiments described above. Modifications and variations of the invention as herein set forth can be made without departing from the spirit and scope thereof, and, therefore, only such limitations should be imposed as are indicated by the appended claims.

Figure 4:
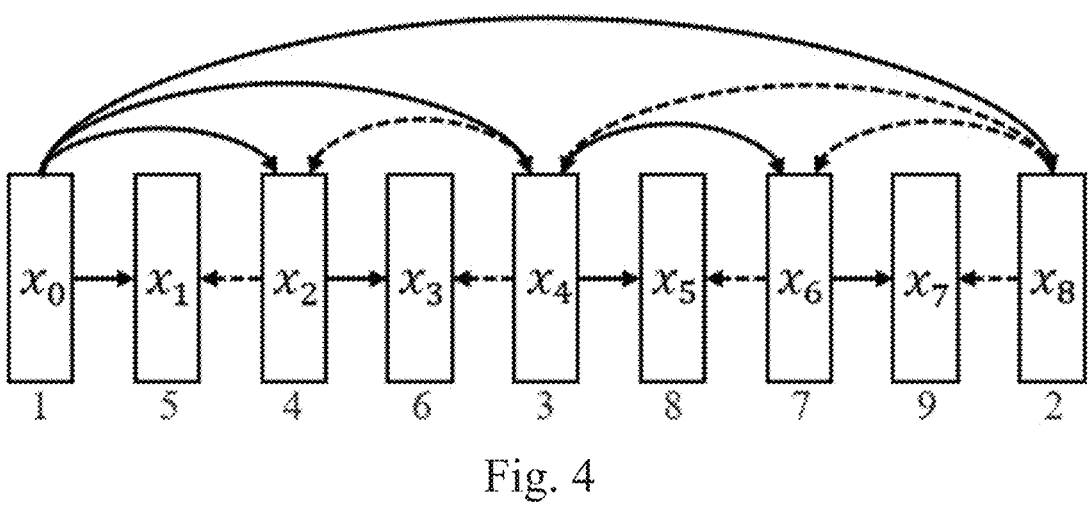
FIG. 4 is an illustration of the hierarchical B-frames coding structure [60], where numbers at the bottom of the figure represent the coding order, solid lines represent the forward reference relationship, and dashed lines represent backward reference relationship.

For example, while the example hierarchical-B coding structure in the embodiment of FIG. 4 includes nine images/slices, other hierarchical-B coding structure in other embodiments may include different number of images/slices.

The systems and/or methods of this disclosure may be applied for use in processing other 3D images (e.g., non-medical images) and/or their associated slices.

What is claimed is:

1. A method for compressing a 3D medical image, comprising the steps:
   a) receiving a 3D medical image;
   b) partitioning the 3D medical image into a plurality of first slices;
   c) encoding the plurality of first slices by a lossy codec into first bitstreams;
   d) decoding the first bitstreams by the lossy codec to obtain a plurality of second slices;
   e) computing a plurality of residues by comparing the plurality of first slices and the plurality of second slices; each said residue corresponding to one said first slice and its corresponding second slice;
   f) encoding the plurality of residues by a lossless codec based on intra-slice bilateral contexts and inter-slice bilateral contexts to obtain a plurality of encoded residues;
   g) outputting the first bitstreams and the plurality of encoded residues as compressed image data.

2. The method of claim 1, wherein step b) further comprises partitioning the 3D medical image along an axis general perpendicular to a partition plane.

3. The method of claim 1, wherein the lossy codec is selected from the group consisting Versatile Video Coding (VVC), High Efficiency Video Coding (HEVC), H.264/MPEG-4 AVC, and Audio Video coding Standard (AVS).

4. The method of claim 1, wherein step f) further comprises:
   h) obtaining bi-directional references for at least some of the plurality of residues; and
   i) extracting the inter-slice bilateral contexts from the bi-directional references and the plurality of second slices.

5. The method of claim 4, wherein step i) further comprises:
   j) applying residual blocks to the bi-directional references and the plurality of second slices to obtain inter-slice features;
   k) processing the inter-slice features by a bi-directional cross-attention module to generate inter-slice reference information; and
   l) Further processing the inter-slice reference information to obtain the inter-slice bilateral contexts.

6. The method of claim 5, wherein step l) further comprises normalizing and concatenating the inter-slice reference information, and feeding the inter-slice reference information to a feed-forward network to generate the inter-slice bilateral contexts.

7. The method of claim 1, wherein step f) further comprises:
   m) extracting intra-slice features from the plurality of second slices; and
   n) processing the intra-slice features by a symmetry-based intra-slice context extraction (SICE) module to generate the intra-slice contexts.

8. The method of claim 7, wherein step n) is conducted by the SICE based on local-symmetric properties of tissues.

9. The method of claim 8, wherein step n) further comprises aggregating neighborhood information in the intra-slice features to obtain local symmetry.

10. The method of claim 7, wherein step n) is conducted by the SICE based on inherent anatomical symmetry of a human body.

11. The method of claim 10, wherein step n) further comprises obtaining long-range correlations in the intra-slice features to obtain global symmetry.

12. The method of claim 1, wherein step g) further comprises merging the first bitstreams and the plurality of encoded residues into a data file or into data streams.

13. The method of claim 4, wherein the bi-directional references are obtained using a hierarchical-B coding structure.

14. The method of claim 1, wherein step f) further comprises:

o) parametrically modelling probability distributions of each of the plurality of residues based on the inter-slice contexts and the intra-slice contexts; and p) encoding the plurality of residues using an arithmetic coding algorithm based on the probability distributions to generate the plurality of encoded residues.

15. A method for decompressing compressed image data to obtain a 3D medical image, comprising the steps:

a) receiving compressed image data;

b) extracting first bitstreams and second bitstreams from the compressed image data;

c) decoding the second bitstreams by a lossless codec based on intra-slice bilateral contexts and inter-slice bilateral contexts to obtain a plurality of residues;

d) decoding the first bitstreams by a lossy codec to obtain a plurality of second slices;

e) adding the plurality of residues to the plurality of second slices to obtain a plurality of first slices; for each of the plurality of second slices a corresponding of the plurality of residues being added thereto; and f) combining the plurality of first slices to obtain a 3D medical image.

16. A system for processing a medical image, comprising:

a) one or more processors; and b) memory storing one or more programs configured to be executed by the one or more processors, the one or more programs including instructions for performing or facilitating performing the method of claim 1.

17. A non-transitory computer-readable storage medium storing one or more programs configured to be executed by one or more processors, the one or more programs including instructions for performing or facilitating performing the method of claim 1.

* * * * *